US008492538B1

(12) United States Patent
Matos

(10) Patent No.: US 8,492,538 B1
(45) Date of Patent: Jul. 23, 2013

(54) CYCLODEXTRIN DERIVATIVE SALTS

(76) Inventor: Jose R. Matos, Plano, TX (US)

(*) Notice: Subject to any disclaimer, the term of this patent is extended or adjusted under 35 U.S.C. 154(b) by 248 days.

(21) Appl. No.: 12/792,385

(22) Filed: Jun. 2, 2010

Related U.S. Application Data

(60) Provisional application No. 61/304,917, filed on Feb. 16, 2010, provisional application No. 61/292,551, filed on Jan. 6, 2010, provisional application No. 61/184,266, filed on Jun. 4, 2009.

(51) Int. Cl.
*C08B 37/16* (2006.01)
*A61K 47/40* (2006.01)

(52) U.S. Cl.
USPC .................. 536/46; 536/103; 514/58

(58) Field of Classification Search
None
See application file for complete search history.

(56) References Cited

U.S. PATENT DOCUMENTS

| | | |
|---|---|---|
| 3,426,011 A | 2/1969 | Parmeter |
| 3,453,257 A | 7/1969 | Parmeter |
| 3,453,258 A | 7/1969 | Parmeter |
| 4,582,900 A | 4/1986 | Brandt et al. |
| 4,638,058 A | 1/1987 | Brandt |
| 4,738,923 A | 4/1988 | Ammeraal |
| 4,920,214 A | 4/1990 | Friedman |
| 5,019,562 A | 5/1991 | Folkman |
| 5,134,127 A | 7/1992 | Stella |
| 5,183,809 A | 2/1993 | Weisz |
| 5,241,059 A | 8/1993 | Yoshinaga |
| 5,376,645 A | 12/1994 | Stella et al. |
| 5,393,880 A | 2/1995 | Shieh et al. |
| 5,512,665 A | 4/1996 | Uchiyama |
| 5,536,826 A | 7/1996 | Hirsenkorn |
| 5,569,756 A | 10/1996 | Qi et al. |
| 5,578,719 A | 11/1996 | Gadelle |
| 5,594,125 A | 1/1997 | Seyschab |
| 5,620,872 A | 4/1997 | Shieh |
| 5,658,894 A | 8/1997 | Weisz |
| 5,760,015 A | 6/1998 | Joullie |
| 5,846,954 A | 12/1998 | Joullie |
| 5,874,418 A | 2/1999 | Stella et al. |
| 6,033,573 A | 3/2000 | Toles |
| 6,046,177 A | 4/2000 | Stella |
| 6,153,746 A | 11/2000 | Shah |
| 6,337,302 B1 | 1/2002 | Teng |
| 6,479,467 B1 | 11/2002 | Buchanan et al. |
| 6,524,595 B1 | 2/2003 | Perrier et al. |
| 6,610,671 B2 | 8/2003 | Buchanan |
| 6,683,087 B2* | 1/2004 | Wikstrom et al. ............ 514/290 |
| 7,034,013 B2 | 4/2006 | Thompson |
| 7,252,791 B2 | 8/2007 | Wasserscheid et al. |
| 2003/0055023 A1 | 3/2003 | Rajewski |
| 2005/0164986 A1 | 7/2005 | Mosher |
| 2006/0258537 A1* | 11/2006 | Stella et al. .................. 504/291 |
| 2009/0011037 A1 | 1/2009 | Pipkin |
| 2009/0012042 A1* | 1/2009 | Ren et al. ........................ 514/58 |
| 2009/0123540 A1 | 5/2009 | Pipkin |

FOREIGN PATENT DOCUMENTS

| | | |
|---|---|---|
| EP | 1950227 A1 | 7/2008 |
| JP | 01-1128063 A | 5/1989 |
| JP | 05-001102 A | 1/1993 |
| JP | 06-206906 * | 7/1994 |
| WO | 91/13100 A1 | 9/1991 |
| WO | 01/40316 A | 6/2001 |
| WO | 2005/042584 A2 | 5/2005 |
| WO | 2005/104712 A2 | 11/2005 |
| WO | 2005/050075 A1 | 5/2007 |
| WO | WO 2007/051358 * | 5/2007 |
| WO | 2009/018069 A2 | 2/2009 |

OTHER PUBLICATIONS

Berge, S. et al "Pharmaceutical Salts" J. Pharm. Sci. (1977) vol. 66, No. 1, pp. 1-19.*
Adam et al. "Cyclodextrin derived hos molecules as reversal agents for the neuromuscular blocker rocuronium bromide: synthesis and structure-activity relationships". J. Med. Chem (2002) 45:1806-1816.
Tarver et al. "2-O-substituted cyclodextrins as reversal agents for the neuromuscular blocker rocuronium bromide". Bioorganic Med. Chem. (2002) 10:1819-1827.
Tongiani et al. "Sulfoalkyl ether-alkyl ether cyclodextrin derivatives, their synthesis, NMR Characterization, and binding of 6alpha-methylprednisolone" J. Pharm. Sci. (Nov. 2005) 94(11):2380-92.
Lammers et al. "Properties of Cyclodextrins". Die Starke (Jan. 1971), 1(5):167-171.
Qu et al. "sulfoalkyl ether beta-cyclodextrin derivatives: synthesis and characterization". J. Inclusion Phenom. Macrocycl. Chem. (2002), 43:213-221.

* cited by examiner

*Primary Examiner* — Leigh Maier
(74) *Attorney, Agent, or Firm* — Rick Matos; Innovar, L.L.C.

(57) ABSTRACT

Chiral salts comprising anionic cyclodextrin derivatives with particular types of non-metal cations are provided. The anionic CD derivative salts can serve as ionic liquids and can possess substantial advantages over currently commercially available ionic liquids particularly for use as chiral phase transfer catalyst, chiral reaction medium, chiral extraction medium, and/or as chiral additive to a chemical process. Methods of preparing the same are provided.

21 Claims, No Drawings

CYCLODEXTRIN DERIVATIVE SALTS

CROSS-REFERENCE TO EARLIER FILED APPLICATIONS

The present application is a non-provisional of and claims the benefit of U.S. Provisional Applications No. 61/304,917, filed Feb. 16, 2010, No. 61/292,551, filed Jan. 6, 2010, and No. 61/184,266, filed Jun. 4, 2009, the entire disclosures of which are hereby incorporated by reference.

FIELD OF THE INVENTION

The present invention relates to compositions comprising ionic cyclodextrin derivatives and cations and to methods for their preparation and use.

BACKGROUND OF THE INVENTION

Anionic and cationic water soluble cyclodextrin derivatives salts can be made according to: 1) Japanese Patent No. JP 05001102 to Yoshinaga (sulfonic acid derivatives of cyclodextrins); 2) U.S. Pat. No. 5,241,059 to Yoshinaga (cyclodextrin derivatives containing sulfoalkyl ether (SAE), ammonium, phosphoric, carboxyl, hydroxyl, tosyl, t-butyl-dimethylsilyl (TBDMS), azide, trimethyl ammonium, or carboxyalkyl ether); 3) PCT International Publication No. WO 01/40316 to Zhang et al. (6-mercapto-cyclodextrin derivatives of the general formula CD-6-O—$CH_2$—S—R—X, wherein R can be an alkylene group and X can be an —$SO_3H$ group, and the cyclodextrin can be α, β, or γ); 4) Adam et al. (*J. Med. Chem.* (2002), 45, 1806-1816) (CD derivatives containing sulfoalkyl (sulfomethyl, sulfoethyl, sulfopropyl)thio ether); 5) Tarver et al. (*Bioorganic & Medicinal Chemistry* (2002), 10, 1819-1827) (sulfoalkyl (sulfoethyl)thioalkyl ether cyclodextrin derivatives); 6) U.S. Pat. No. 5,594,125 to Seyschab (cyclodextrin derivatives having at least one lipophilic substituent and one hydrophilic radical per cyclodextrin molecule); 7) U.S. Pat. No. 5,760,015 and No. 5,846,954 to Joullie ("one-sided" water soluble cyclodextrin derivatives having at least 10 anionic groups on one side of the CD molecule); 8) U.S. Pat. No. 5,019,562 to Folkman (anionic CD derivatives having a sulfate, phosphate, or carboxylate group); 9) U.S. Pat. No. 5,183,809 to Weisz et al. (polyionic derivatives having a sulfate, phosphate, carboxylate or nitrate group); 10) U.S. Pat. No. 5,658,894 to Weisz et al. (polymeric CD derivatives, wherein the CD comprises anionic R groups selected from the group consisting of sulfate, phosphate, sulfonate, carboxylate and nitrate, and nonanionic R groups selected from the group consisting of H, alkyl, aryl, ester, ether, thioester, thioether); 11) European Publication No. 01950227 to Ren et al. (Hydroxypropyl ether-sulfobutyl ether cyclodextrin derivatives), all of the disclosures of which are hereby incorporated by reference.

Sulfoalkyl ether cyclodextrin (SAE-CD) derivatives are polyanionic, hydrophilic, water soluble cyclodextrins derivatized with sulfoalkyl ether functional groups. SAE-CD derivatives are commercially available from CyDex Pharmaceuticals, Inc. (Lenexa, Kans.). SAE-CD is currently marketed under the trademarks Captisol® and Advasep®. SAE-CD can be manufactured according to the process disclosed in U.S. Pat. No. 6,153,746 to Pfizer, Inc.

Captisol® has an average of about 7 sulfoalkyl ether substituents per cyclodextrin molecule. The anionic sulfobutyl ether substituent dramatically improves the aqueous solubility and safety of the parent cyclodextrin. Reversible, non-covalent, complexation of drugs with CAPTISOL® generally allows for increased solubility and, in some cases, increased stability of drugs in aqueous solutions.

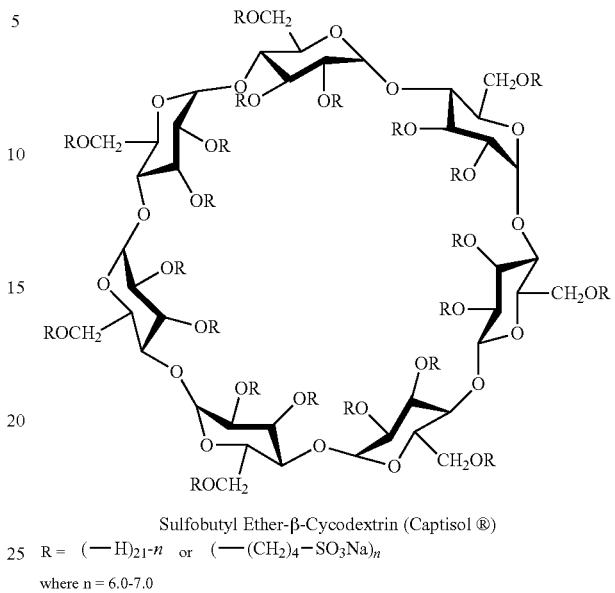

Sulfobutyl Ether-β-Cycodextrin (Captisol ®)

$R = (-H)_{21-n}$ or $(-(CH_2)_4-SO_3Na)_n$ where n = 6.0-7.0

Various embodiments of a sulfoalkyl ether cyclodextrin include eicosa-O-(methyl)-6G-O-(4-sulfobutyl)-β-cyclodextrin, heptakis-O-(sulfomethyl)-tetradecakis-O-(3-sulfopropyl)-β-cyclodextrin, heptakis-O-[1,1-dimethylethyl)dimethylsilyl]-tetradecakis-O-(3-sulfopropyl)-β-cyclodextrin, heptakis-O-(sulfomethyl)-tetradecakis-O-(3-sulfopropyl)-β-cyclodextrin, and heptakis-O-[1,1-dimethylethyl)dimethylsilyl]-tetradecakis-O-(sulfomethyl)-β-cyclodextrin. Other known ether cyclodextrin derivatives containing a sulfoalkyl moiety include sulfoalkylthio and sulfoalkylthioalkyl ether derivatives such as octakis-(S-sulfopropyl)-octathio-γ-cyclodextrin, octakis-O-[3-[2-sulfoethyl)thio]propyl]-β-cyclodextrin], and octakis-S-(2-sulfoethyl)-octathio-γ-cyclodextrin.

The preparation of SAE-CD derivatives is disclosed in U.S. Pat. No. 5,376,645 and No. 5,134,127 to Stella et al. The SAE-CD derivatives or CD derivatives containing a sulfonate functional group can also be made according to Parmerter et al. (U.S. Pat. No. 3,426,011), Gadelle et al. (U.S. Pat. No. 5,578,719), Joullie et al. (U.S. Pat. No. 5,760,015 and U.S. Pat. No. 5,846,954), Buchanan et al. (U.S. Pat. No. 6,610,671 and U.S. Pat. No. 6,479,467), Perrier et al. (U.S. Pat. No. 6,524,595), Uchiyama et al. (U.S. Pat. No. 5,512,665), Lammers et al. (*Recl. Trav. Chim. Pays-Bas* (1972), 91(6), 733-742); Staerke (1971), 23(5), 167-171), Qu et al. (*J. Inclusion Phenom. Macro. Chem.*, (2002), 43, 213-221), Yoshinaga (Japanese Patent No. JP 05001102; U.S. Pat. No. 5,241,059), Zhang et al. (PCT International Publication No. WO 01/40316), Adam et al. (*J. Med. Chem.* (2002), 45, 1806-1816), Tarver et al. (*Bioorganic & Medicinal Chemistry* (2002), 10, 1819-1827), Matos et al. (PCT International Publication No. WO 09/18069), Pipkin et al. (PCT International Publications No. WO 05/104712 and No. 07/50075), and Shah et al. (U.S. Pat. No. 6,153,746), the entire disclosures of which are hereby incorporated by reference.

Water soluble cyclodextrin derivatives can also be made according to: 1) Japanese Patent No. JP 05001102 to Yoshinaga (sulfonic acid derivatives of cyclodextrins); 2) U.S. Pat. No. 5,241,059 to Yoshinaga (cyclodextrin derivatives containing sulfoalkyl ether (SAE), ammonium, phosphoric, carboxyl, hydroxyl, tosyl, t-butyl-dimethylsilyl (TBDMS), azide, trimethyl ammonium, or carboxyalkyl ether); 3) PCT International Publication No. WO 01/40316 to Zhang et al. (6-mercapto-cyclodextrin derivatives of the general formula CD-6-O—CH$_2$—S—R—X, wherein R can be an alkylene group and X can be an —SO$_3$H group, and the cyclodextrin can be α, β, or γ); 4) Adam et al. (*J. Med. Chem.* (2002), 45, 1806-1816) (CD derivatives containing sulfoalkyl (sulfomethyl, sulfoethyl, sulfopropyl)thio ether); 5) Tarver et al. (*Bioorganic & Medicinal Chemistry* (2002), 10, 1819-1827) (sulfoalkyl (sulfoethyl)thioalkyl ether cyclodextrin derivatives); 6) U.S. Pat. No. 5,594,125 to Seyschab (cyclodextrin derivatives having at least one lipophilic substituent and one hydrophilic radical per cyclodextrin molecule); 7) U.S. Pat. No. 5,760,015 and U.S. Pat. No. 5,846,954 to Joullie ("one-sided" water soluble cyclodextrin derivatives having at least 10 anionic groups on one side of the CD molecule); 8) U.S. Pat. No. 5,019,562 to Folkman (anionic CD derivatives having a sulfate, phosphate, or carboxylate group); 9) U.S. Pat. No. 5,183,809 to Weisz et al. (polyionic derivatives having a sulfate, phosphate, carboxylate or nitrate group); 10) U.S. Pat. No. 5,658,894 to Weisz et al. (polymeric CD derivatives, wherein the CD comprises anionic R groups selected from the group consisting of sulfate, phosphate, sulfonate, carboxylate and nitrate, and nonanionic R groups selected from the group consisting of H, alkyl, aryl, ester, ether, thioester, thioether); 11) alkyl ether derivatized cyclodextrins (AE-CD's) (see Fromming and Szejtli, Cyclodextrins in Pharmacy, Kluwer Academic Publishing, Dordrecht, 1994 and references therein); 12) U.S. Pat. No. 5,536,826 to Hirsenkorn or U.S. Pat. No. 4,638,058 to Brandt et al. (aminoalkyl ether cyclodextrin (AAE-CD) derivatives), the entire disclosures of all the above being hereby incorporated by reference.

All of the currently available forms of anionic CD derivatives include metal salts and amine (non-quaternary amine) salts. Some SAE-CD salts include cations selected from the group consisting of alkali metals (e.g. Li$^+$, Na$^+$, K$^+$), alkaline earth metals (e.g., Ca$^{+2}$, Mg$^{+2}$), and amine cations such as the cations of ($C_1$-$C_6$)-alkylamines, piperidine, pyrazine, ($C_1$-$C_6$)-alkanolamine, ethylenediamine, and ($C_4$-$C_8$)-cycloalkanolamine. Quaternary amine salts of anionic water soluble cyclodextrin derivatives have not been prepared.

Salts comprising a quaternary ammonium cation and a sulfate-based or sulfonate-based anion are known: PCT International Application Serial No. PCT/EP02/10206 filed Sep. 11, 2002 and published as PCT International Publication No. WO 03/022812 on Mar. 20, 2003; U.S. application Ser. No. 10/930,674 and Ser. No. 11/262,941.

The term "ionic liquids" has been understood to mean salts or mixtures of salts whose melting point is below 100° C. (P. Wasserscheid, W. Keim, *Angew. Chem.* 2001, 112, 3926); however, such a definition is not absolute. Exemplary ionic liquids include anions, such as halogenostannates, halogenoaluminates, hexafluorophosphates or tetrafluoroborates combined with substituted ammonium cations, phosphonium cations, pyridinum cations or imidazolium cations to thereby form salts. The use of ionic liquids in synthetic reactions has been described by Wasserscheid et al. (Ionic Liquids in Synthesis; eds. Peter Wasserscheid, Thomas Welton, 2003, Wiley-VCH Verlag GmbH & Co. KGaA, Germany). Several publications have already described the use of ionic liquids as solvents for chemical reactions (T. Welton, Chem. Rev. 1999, 99, 2071; P. Wasserscheid, W. Keim, *Angew. Chem.*, 2000, 112, 3926). For example, hydrogenation reactions of olefins with rhodium(I) (P. A. Z. Suarez, J. E. L. Dullius, S. Einloft, R. F. de Souza and J. Dupont, *Polyhedron* 15/7, 1996, 1217-1219), ruthenium(II) and cobalt(II) complexes (P. A. Z. Suarez, J. E. L. Dullius, S. Einloft, R. F. de Souza and J. Dupont, *Inorganica Chimica Acta* 255, 1997, 207-209) have been carried out successfully in ionic liquids with tetrafluoroborate anion. The hydroformylation of functionalized and non-functionalized olefins is possible with rhodium catalysts in ionic liquids with weakly coordinating anions (e.g. PF$_6^-$, BF$_4^-$) (Y. Chauvin, L. Mussmann, H. Olivier, European Patent, EP 776880, 1997; Y. Chauvin, L. Mussmann, H. Olivier, *Angew. Chem., Int. Ed. Engl.,* 1995, 34, 2698; W. Keim, D. Vogt, H. Waffenschmidt, P. Wasserscheid, *J. of Cat.,* 1999, 186, 481).

Ionic liquids can also be used as extraction agents (solvents) for material separation (J. G. Huddleston, H. D. Willauer, R. P. Swatloski, A. E. Visser, R. D. Rogers, *Chem. Commun.* 1998, 1765-1766; b) A. E. Visser, R. P. Swatlowski, R. D. Rogers, *Green Chemistry* 2000, 2(1), 1-4) and as heat carriers (M. L. Mutch, J. S. Wilkes, *Proceedings of the Eleventh International Symposium on Molten Salts*, P. C. Trulove, H. C. De Long, G. R. Stafford and S. Deki (Hrsg.), Proceedings Volume 98-11, The Electrochemical Society, Inc, Pennington, N.J.; 1998, page 254).

SUMMARY OF THE INVENTION

The inventor has unexpectedly discovered that chiral salts can be made from anionic cyclodextrin derivatives and quaternary nitrogen-containing cations. The compositions can be made via an ion exchange process or by direct derivatization or quaternization. A chiral salt can be used as chiral phase transfer catalyst, chiral reaction medium, chiral extraction medium, and/or as chiral additive to a chemical process. In some embodiments, the chiral salt is a chiral ionic liquid.

The chiral salt of the invention comprises: 1) a chiral anion and an achiral cation; 2) an achiral anion and a chiral cation; or 3) a chiral anion and a chiral cation. A chiral cation is a cationic molecule possessing one or more chiral centers. A chiral anion is an anionic molecule possessing one or more chiral centers. An anion can contain one or more anionic functional groups. A cation can contain one or more cationic functional groups.

In some embodiments, the chiral anion is an anionic cyclodextrin (CD) derivative. In some embodiments, the anionic cyclodextrin derivative is a sulfoalkyl ether derivatized CD, sulfonate derivatized CD, sulfate derivatized CD, sulfated alkyl derivatized CD, carboxyalkyl ether derivatized CD, succinylate derivatized CD, sulfoalkylthio ether derivatized CD, sulfoalkyl ether-alkyl ether derivatized CD, sulfoalkyl ether-hydroxyalkyl ether derivatized CD, carboxylate derivatized CD, phosphoalkyl derivatized CD, phosphate derivatized CD, phosphonate derivatized CD, carboxyalkyl ether-alkyl ether derivatized CD, or a combination thereof.

In some embodiments, the cation is a non-metal cation, such as a phosphonium cation or a quaternary nitrogen-containing cation. A quaternary nitrogen-containing cation is a cationic aromatic or cationic non-aromatic molecule containing a quaternized nitrogen atom embedded within an aromatic heterocycle, a non-aromatic heterocycle, an alkane, an alkene or an alkyne. The nitrogen atom can be substituted with one or more R, $R_1$, $R_2$, $R_3$, $R_4$, $R_5$, or $R_6$ groups independently selected at each occurrence from those defined herein in order to render the nitrogen cationic (quaternary).

In some embodiments, the cation is a cationic aromatic heterocycle independently selected at each occurrence from the group consisting of acridinium, azocinium, benzimidazolium, benzotriazolinium (benztriazolinium), borazinium, cinnolinium, 1,2-diazepinium, 1,3-diazepinium, 1,4-diazepinium, benzo-1,2-diazepinium, benzo-1,3-diazepinium, benzo-1,4-diazepinium, benzoxazinium, carbazolium, imidazolium, isoquinolinium, indazolium, indolium, isoindolium, nicotinium, 1,2,5-oxadiazolinium (furazanium), oxazinium, pentazolium, phenanthridinium, phenanthrolinium, purinium, pyrimidinium, pyridazinium, pteridinium, purinium, pyridinium, pyrazinium, pyrazolium, pyrrolium, quinoxalinium, quinolinium, quinazolinium, terpyridinium, thiazepinium, thiazinium, thiazolium, triazinium, and triazolinium, wherein a (the) nitrogen atom in the aromatic heterocycle is substituted with one or more R, $R_1$, $R_2$, $R_3$, $R_4$, $R_5$, or $R_6$ groups independently selected at each occurrence from those defined herein in order to render the nitrogen cationic.

In some embodiments, the cation is a cationic non-aromatic heterocycle independently selected at each occurrence from the group consisting of azetinium, azatadinium, azepanium, azocanium, hexamonium, indolinium, imidazolinium, morpholinium, oxazolidinium, isoxazolidinium, pentazolinium, piperidinium, piperazinium, pyrazolidinium, pyrrolinium, thiazolidinium, thiazolinium, pyrrolidinium, quinolizidinium, pyrrolizinium, 1,4,7-triazacyclononanium, and 1,4,7,10-tetrazacyclododecanium, wherein a(the) nitrogen atom in the non-aromatic heterocycle is substituted with one or more R, $R_1$, $R_2$, $R_3$, $R_4$, $R_5$, or $R_6$ groups independently selected at each occurrence from those defined herein in order to render the nitrogen cationic.

In some embodiments, the non-metal cation is independently selected at each occurrence from the group consisting of quaternary ammonium cation, imidazolium cation, pyridinium cation, pyrazolium cation, guanidinium cation, phosphonium cation, and triazolium cation, wherein at least one nitrogen atom in the cation is substituted with one or more R, $R_1$, $R_2$, $R_3$, $R_4$, $R_5$, or $R_6$ groups independently selected at each occurrence from those defined herein in order to render the nitrogen cationic. In some embodiments, the cation excludes a metal cation, a primary amine cation, a secondary amine cation, and/or a tertiary amine cation.

In some embodiments, the chiral salt of the invention is pure or contains less than 0.1%, less than 0.5%, less than 1%, less than 5%, less than 10%, less than 20%, less than 30%, less than 40% or less than 50% or another compound.

In some embodiments, the chiral salt of the invention containing a non-metal cation is less water soluble than a corresponding salt wherein the cation is a metal cation. In some embodiments, the chiral salt of the invention containing a non-metal cation is more soluble in organic solvent than it is in water. In some embodiments, the chiral salt of the invention containing a non-metal cation possesses a water solubility at room temperature of less than 500 mg/mL, less than 300 mg/mL, less than 250 mg/mL, less than 200 mg/mL, less than 150 mg/mL, less than 100 mg/mL, less than 50 mg/mL or less than 25 mg/mL. In some embodiments, the chiral salt of the invention containing a non-metal cation possesses a water solubility at room temperature of greater than 0.1 mg/mL, greater than 0.5 mg/mL, greater than 1 mg/mL, greater than 5 mg/mL, greater than 10 mg/mL or greater than 20 mg/mL. In some embodiments, the chiral salt of the invention containing a non-metal cation is insoluble or poorly soluble (less than 250 mg/mL, less than 200 mg/mL, less than 100 mg/mL, 50 mg/mL, less than 25 mg/mL or less than 10 mg/mL) in non-polar or moderately polar organic solvent. In some embodiments, the invention provides ionic liquids containing combinations of the above solubility properties.

In some embodiments, the cation present in the chiral salt comprises a combination of metal cation and non-metal cation. A metal cation can be an alkali metal cation (e.g. $Li^+$, $Na^+$, $K^+$), an alkaline earth metal cation (e.g., $Ca^{+2}$, $Mg^{+2}$), a transition metal cation (cations of Sc, Ti, V, Cr, Mn, Fe, Co, Ni, Cu, Zn, Y, Zr, Nb, Mo, Tc, Ru, Rh, Rd, Ag, Cd, Hf, Ta, W, Re, Os, Ir, Pt, Au or Hg) or other such cationic metal. In some embodiments, the chiral salt comprises a mixture metal cation and non-metal cation. (See Example 15)

In some embodiments, the cation is chiral, and the chiral cation is independently selected at each occurrence from a chiral quaternary ammonium, chiral imidazolium, chiral pyridinium, chiral pyrazolium, chiral guanidinium, chiral phosphonium cation and chiral triazolium cation, each cation being independently substituted or unsubstituted. In some embodiments, the chiral cation is a chiral cationic cyclodextrin (CD) derivative. In some embodiments the chiral cationic cyclodextrin derivative is a quaternary ammonium derivatized CD, imidazolium derivatized CD, pyridinium derivatized CD, pyrazolium derivatized CD, guanidinium derivatized CD, triazolium derivatized CD or a combination thereof.

In some embodiments, the anion is an achiral or chiral anion selected from the group consisting of a derivatized sulfate, derivatized sulfonate, derivatized carboxylate, derivatized succinate, derivatized phosphate, derivatized phosphonate, or combination thereof. In some embodiments, the anion is an achiral or chiral anion selected from the group consisting of an alkyl sulfonate, alkyl sulfate, thioalkyl sulfonote, alkylcarboxylate, alkylphosphonate, alkylphosphate, or a combination thereof, wherein "alkyl" is defined as herein.

The "alkyl" group(s) herein can be a linear or branched, saturated or unsaturated, aliphatic or alicyclic alkyl radical with 1-36 or 3-36 carbon atoms. The alkyl group is non-functionalized or otherwise functionalized with one or more groups selected from the group consisting of an —OH, —OR", —COOH, —COOR", —SO$_4$, —F, —Cl, —Br, —I or —CN, wherein R" is selected from the group consisting of a branched or linear hydrocarbon chain with 1-12 carbon atoms. The "alkyl" group is independently selected at each occurrence.

The invention also provides a method of using a chiral salt according to the invention as a chiral phase transfer catalyst, chiral reaction medium, chiral extraction medium and/or as chiral additive in a chemical process. In some embodiments, the process is a batch-type process, semi-continuous process or continuous process. In some embodiments, the process is operated in co-current or counter-current mode.

Some embodiments of the invention provide an extraction process comprising: a) exposing a solid or liquid comprising at least one compound to be extracted to an extraction phase comprising chiral salt of the invention, wherein the at least one compound is a mixture of Isomer-1 and Isomer-2 of enantiomers or diastereomers, and the chiral salt comprises an anionic cyclodextrin derivative and a quaternary nitrogen-containing cation; b) mixing the solid or liquid with the extraction phase for a period of time sufficient to specifically or selectively extract a first portion of Isomer-1 into the extraction phase; c) separating the extraction phase from the solid or liquid; and d) separating the extracted first portion of Isomer-1 from the extraction phase to provide an enantiomerically enriched, enantiomerically pure, diastereomerically-enriched or diastereomerically-pure Isomer-1 of the compound. In some embodiments, the liquid is an aqueous liquid phase or an organic liquid phase that is immiscible or partially miscible (less than 1% wt., less than 5% wt., less than 10% wt. or less than 20% wt. miscibility) with the extraction phase. In some embodiments, the at least one compound to be extracted is present in an aqueous liquid phase or an organic liquid phase. In some embodiments, the solid or liquid excludes water. In some embodiments, the extraction phase excludes water. In some embodiments, the extraction phase has less a solubility, in the organic liquid phase, of less than 50% wt., less than 40% wt., less than 30% wt., less than 20% wt., less than 10% wt., less than 5% wt., less than 2% wt. or less than 1% wt.

In some embodiments, the ratio of Isomer-1 to Isomer-2 in the compound prior to extraction approximates 1/1 and, after extraction, is less than 1/1, less than 1/1.2, less than 1/1.5, less than 1/1.75, less than 1/2, less than 1/2.5, less than 1/3, less than 1/4, less than 1/5, less than 1/6, less than 1/7, less than 1/8, less than 1/9, less than 1/9.5, less than 1/9.9, less than 1/10, less than 1/15, less than 1/20, less than 1/50 or less than 1/100 for the compound not extracted into the extraction phase. In some embodiments, the ratio of Isomer-1 to Isomer 2 in the enantiomerically-enriched or diastereomerically-enriched compound is greater than 1/1, greater than 1.5/1, greater than 2/1, greater than 3/1, greater than 4/1, greater than 5/1, greater than 6/1, greater than 7/1, greater than 8/1, greater than 9/1, greater than 9.5/1, greater than 9.9/1, greater than 10/1, greater than 20/1, greater than 50/1 or greater than 100/1.

In some embodiments, the ratio of $K_1/K_2$, wherein K1 is the binding constant for complexation of Isomer-1 (or "structurally related compound") with the anionic cyclodextrin in the chiral salt and K2 is the binding constant for complexation of Isomer-2 (or another "structurally related compound") with the anionic cyclodextrin in the chiral salt, exceeds 1/1, 2/1, 3/1, 5/1, 10/1, 20/1, 50/1, 100/1, 200/1, 500/1, 1000/1, 5000/or 10000/1.

In some embodiments, the moles of chiral salt in the extraction phase approximate or are less than the moles of Isomer-1 (or "structurally related compound) in the mixture. In some embodiments, the moles of chiral salt in the extraction phase are greater than the moles of Isomer-1 (or "structurally related compound) in the mixture. In some embodiments, the molar ratio of chiral salt to Isomer-1 approximates 1/1 is less than 1/1, less than 1/1.2, less than 1/1.5, less than 1/1.75, less than 1/2, less than 1/2.5, less than 1/3, less than 1/4, less than 1/5, less than 1/6, less than 1/7, less than 1/8, less than 1/9, less than 1/9.5, less than 1/9.9, less than 1/10, less than 1/15, less than 1/20, less than 1/50 or less than 1/100. In some embodiments, the molar ratio of chiral salt to Isomer-1 is greater than 1/1, greater than 1.5/1, greater than 2/1, greater than 3/1, greater than 4/1, greater than 5/1, greater than 6/1, greater than 7/1, greater than 8/1, greater than 9/1, greater than 9.5/1, greater than 9.9/1, greater than 10/1, greater than 20/1, greater than 50/1 or greater than 100/1.

In some embodiments, the invention provides a supercritical fluid extraction process for the separation of one or more target compounds from a mass comprising the one or more target compounds, the process comprises: a) providing a solid or liquid mass comprising one or more target compounds; b) treating the mass with an ionic liquid and a supercritical fluid to form an ionic liquid phase and a supercritical fluid phase; c) separating the supercritical fluid phase from the ionic liquid phase; and d1) isolating the one or more target compounds from the supercritical fluid phase by removal of the supercritical fluid, e.g. evaporation thereof, and/or d2) isolating the one or more target compounds from the ionic liquid phase by treating the ionic liquid with an aqueous or organic phase into which the one or more compounds is extracted. After the step of separating (above in step c)), the process optionally comprises the step of: e) treating the ionic liquid phase after step c) with additional supercritical fluid and subsequently separating the ionic liquid phase from the supercritical fluid phase, then combining two separated supercritical fluid phases of steps c) and e) and then repeating step d1). Any of the steps can be repeated as needed to improve enrichment or purity.

In some embodiments, the invention also provides a method of separating one or more compounds from a mixture of structurally related compounds. "A mixture of structurally related compounds" is a group of compounds sharing a substantial structural similarity for the core structure of each compound in the mixture, wherein the binding constant for complexation, with an anionic cyclodextrin, of one compound in the group is different from the binding constant for complexation, with the same anionic cyclodextrin, of another compound in the group. For example, the group of compounds might be a group of steroids, corticosteroids, adenosteroids, esters, ethers, amino acids, amino acid derivatives, antibiotics, narcotics, prescription drugs, illegal drugs or other such compounds. The method comprises: exposing a solid or liquid containing a mixture of structurally related compounds to an extraction phase containing chiral salt of the invention, wherein the chiral salt comprises an anionic cyclodextrin derivative and a quaternary nitrogen-containing cation; b) mixing the solid or liquid with the extraction phase for a period of time sufficient to specifically or selectively extract one or more compounds from the mixture of structurally related compounds into the extraction phase; c) separating the extraction phase from the solid or liquid; and d) separating the extracted one or more compounds from the extraction phase to provide an enriched or pure one or more compounds. Any of the steps can be repeated as needed to improve enrichment or purity.

Some embodiments of the invention provide an extraction process comprising: a) exposing a solid or liquid containing at least a first compound and a second compound to an extraction phase containing chiral salt of the invention, wherein the chiral salt comprises an anionic cyclodextrin derivative and a quaternary nitrogen-containing cation; b) mixing the solid or liquid with the extraction phase for a period of time sufficient to specifically or selectively extract a first portion of first compound into the extraction phase; c) separating the extraction phase from the solid or liquid; and d) separating the extracted first portion of first compound from the extraction phase to provide an enriched or pure first compound. Any of the steps can be repeated as needed to improve enrichment or purity.

In some embodiments, the ratio of first compound to second compound prior to extraction approximates 1/1 and, after extraction, is less than 1/1, less than 1/1.2, less than 1/1.5, less than 1/1.75, less than 1/2, less than 1/2.5, less than 1/3, less than 1/4, less than 1/5, less than 1/6, less than 1/7, less than 1/8, less than 1/9, less than 1/9.5, less than 1/9.9, less than 1/10, less than 1/15, less than 1/20, less than 1/50 or less than 1/100 for the compound not extracted into the extraction phase. In some embodiments, the ratio of first compound to second compound in the enriched first compound is greater than 1/1, greater than 1.5/1, greater than 2/1, greater than 3/1, greater than 4/1, greater than 5/1, greater than 6/1, greater than 7/1, greater than 8/1, greater than 9/1, greater than 9.5/1, greater than 9.9/1, greater than 10/1, greater than 20/1, greater than 50/1 or greater than 100/1.

In some embodiments, the ratio of $K_{FC}/K_{SC}$ exceeds 1/1, 2/1, 3/1, 5/1, 10/1, 20/1, 50/1, 100/1, 200/1, 500/1, 1000/1, 5000/or 10000/1, wherein $K_{FC}$ is the binding constant for complexation of first compound with the anionic cyclodextrin in the chiral salt and $K_{SC}$ is the binding constant for complexation of second compound with the anionic cyclodextrin in the chiral salt.

In some embodiments, the moles of chiral salt in the extraction phase approximate or are less than the moles of first compound. In some embodiments, the moles of chiral salt in the extraction phase are greater than the moles of first compound. In some embodiments, the molar ratio of chiral salt to first compound approximates 1/1 is less than 1/1, less than 1/1.2, less than 1/1.5, less than 1/1.75, less than 1/2, less than 1/2.5, less than 1/3, less than 1/4, less than 1/5, less than 1/6, less than 1/7, less than 1/8, less than 1/9, less than 1/9.5, less than 1/9.9, less than 1/10, less than 1/15, less than 1/20, less than 1/50 or less than 1/100. In some embodiments, the molar ratio of chiral salt to first compound is greater than 1/1, greater than 1.5/1, greater than 2/1, greater than 3/1, greater than 4/1, greater than 5/1, greater than 6/1, greater than 7/1, greater than 8/1, greater than 9/1, greater than 9.5/1, greater than 9.9/1, greater than 10/1, greater than 20/1, greater than 50/1 or greater than 100/1.

The invention also provides a chemical process comprising: a) providing a chiral salt of the invention as a reaction medium, one or more starting materials and optionally one or more catalysts, wherein the chiral salt comprises an anionic cyclodextrin derivative and a quaternary nitrogen-containing cation; b) mixing the chiral salt, one or more starting materials and optionally one or more catalysts, whereby the one or more starting materials complexes with the chiral salt in situ, to form a reaction milieu, optionally while heating the reaction milieu, cooling the reaction milieu and/or exposing the reaction milieu to radiation, and causing a chemical reaction to form at least one enantiomerically-enriched, enantiomerically-pure, diastereomerically-pure or diastereomerically-enriched reaction product; c) and isolating the reaction product. In some embodiments, the catalyst is present and is independently selected at each occurrence from the group consisting of a base, acid, enzyme, protein, antibody, RNA, polymer and mineral. In some embodiments, water is included in the reaction medium. In some embodiments, the reaction medium comprises an aqueous phase and a chiral salt-containing phase. In some embodiments, the reaction medium comprises a chiral salt-containing phase and an organic liquid phase that is immiscible or partially miscible with the chiral salt-containing phase.

In some embodiments, the chemical reaction is selected from the group consisting of hydrolysis, esterification, oxidation, reduction, hydrogenation, hydroformylation, dimerization, oligomerization, isomerization, amidation, C—C bond formation, alkylation, Friedel-Crafts acylation, Beckmann rearrangement, osmylation, Heck coupling, Henry reaction, Knoevenagel condensation of aliphatic and aromatic carbonyl compounds, acetylation, Diels-Alder reaction, photocyclization or others known in the art of ionic liquid usage in chemical reaction processes.

In some embodiments, the extraction phase or reaction medium comprises at least 5% wt., at least 10% wt., at least 20% wt., at least 30% wt., at least 40% wt., at least 50% wt., at least 60% wt., at least 70% wt., at least 80% wt., at least 90% wt., at least 95% wt., at least 98% wt. or at least 99% wt. of chiral salt of the invention. In some embodiments, the extraction phase or reaction medium, before use, comprises only chiral salt of the invention. In some embodiments, the extraction process or chemical reaction process is conducted in the absence of an aqueous phase, in the absence of water and/or in the absence of an organic solvent. In some embodiments, the extraction or chemical reaction is conducted at ambient temperature, at a temperature ranging from 20° C. to 300° C. or at a temperature above the melting point of the cationic salt of the invention. In some embodiments, the period of time sufficient ranges from 1 min to 4 days, 1 min to 3 days, 1 min to 2 days, 1 min to 24 hours, 1 min to 18 hours, 1 min to 12 hours, 1 min to 6 hours, 1 min to 60 min, 1 hour to 24 hours, 1 hour to 18 hours, 4 hours to 18 hours, or 8 hours to 12 hours.

In some embodiments, the aqueous phase comprises water and one or more additives selected from the group consisting of buffer, inorganic salt, metal halide salt, metal carboxylate salt, complexing agent or a combination thereof.

The invention includes combinations and sub-combinations of the various aspects and embodiments disclosed herein. These and other aspects of this invention will be apparent upon reference to the following detailed description, examples, claims, and attached figures.

DETAILED DESCRIPTION OF THE INVENTION

The chiral salt of the invention possesses unexpected advantages over other salts. In some embodiments, the chiral salt is a chiral ionic liquid. The ionic liquid can be used to conduct chiral selective chemical reactions, conduct chiral specific chemical reactions, conduct chirally-selective extraction, conduct chirally-specific extraction, conduct enzymatic reaction or other such purposes. It can also be used for the same purposes as other known ionic liquids.

As used herein, the term "ionic liquid" refers to a salt of the invention or mixture of salts of the invention whose melting point is below 300° C., below 250° C., below 200° C., below 150° C., below 125° C., or below 100° C. An ionic liquid may be a solid or liquid at 20 to 35° C.

The chiral anion of the instant chiral salt can comprise an anion of the formula 1:

wherein Y is a chiral group and Z is an anionic functional group covalently bound to Y. In some embodiments, Y is a cyclodextrin molecule, meaning the anion has the formula cyclodextrin-$Z_m$. Y can be selected from the group consisting of α-cyclodextrin, β-cyclodextrin, γ-cyclodextrin, maltodextrin, cyclomaltodextrin, cyclomaltohexaose, cyclomaltoheptaose, and cyclomaltooctaose. Accordingly, the cyclodextrin comprises one or more Z groups and zero or more hydroxyl groups. "m" can be: in the range of 1 to 18 when Y is an α-cyclodextrin; in the range of 1 to 21 when Y is a β-cyclodextrin; or in the range of 1 to 24 when Y is γ-cyclodextrin. "Y" optionally further comprises one or more nonionic (neutral) functional groups covalently bound to the CD.

In some embodiments, Z is independently selected at each occurrence from an anionic functional group independently selected at each occurrence from the group of sulfonate, sulfate, carboxylate, sulfalkyl ether, carboxyalkyl ether, phosphate, phosphonate, phosphoalkyl, succinate and a combination thereof.

In some embodiments, the chiral anion is independently selected at each occurrence from the group consisting of sulfoalkyl ether derivatized CD (SAE-CD), sulfated alkyl ether derivatized CD (SFAE-CD) sulfonate derivatized CD (SNT-CD), sulfate derivatized CD (SFT), carboxyalkyl ether derivatized CD (CAE-CD), succinylate derivatized CD (SCN-CD), sulfoalkylthio ether derivatized CD (SATE-CD), sulfoalkyl ether-alkyl ether derivatized CD (SAE-AE-CD), sulfoalkyl ether-hydroxyalkyl ether derivatized CD (SAE-HAE-CD), carboxylate derivatized CD (CXT-CD), phosphoalkyl ether derivatized CD (PAE-CD), phosphate derivatized CD (PHT-CD), phosphonate derivatized CD (PNT-CD), carboxyalkyl ether-alkyl ether derivatized CD (CAE-AE-CD), carboxyalkyl ether-hydroxyalkyl ether derivatized CD (CAE-HAE-CD), and a combination thereof.

The cation can be chiral or achiral. In some embodiments, the cation is independently selected at each occurrence from the group consisting of quaternary ammonium, imidazolium, guanidinium, phosphonium, pyridinium, pyrazolium, and triazolium cation. In some embodiments, the chiral cation is independently selected at each occurrence from the group consisting of a chiral quaternary ammonium, chiral imidazolium, chiral guanidinium, chiral pyridinium, chiral pyrazolium, or chiral triazolium cation. A cation used herein can be substituted at a nitrogen or carbon atom with one or more functional groups selected from the group consisting of R, $R_1$, $R_2$, $R_3$, $R_4$, $R_5$, and $R_6$ as defined herein. Exemplary cations include chiral or achiral forms of:

1) quaternary ammonium cation with the general formula $(NR_1R_2R_3R)^+$;
2) phosphonium cation with the general formula $(PR_1R_2R_3R)^+$;
3) imidazolium cation with the general formula

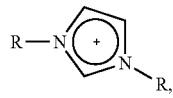

in which the imidazole core may be substituted with at least one group selected from $C_1$-$C_6$ alkyl group, $C_1$-$C_6$ alkoxy group, $C_1$-$C_6$ hydroxyalkyl group, $C_1$-$C_6$ aminoalkyl group, $C_5$-$C_{12}$ aryl group or $C_5$-$C_{12}$-aryl-$C_1$-$C_6$ alkyl group;

4) pyridinium cation with the general formula

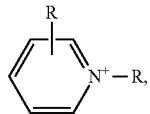

in which the pyridine core may be substituted with at least one group selected from $C_1$-$C_6$ alkyl group, $C_1$-$C_6$ alkoxy group, $C_1$-$C_6$ hydroxyalkyl group, $C_1$-$C_6$ aminoalkyl group, $C_5$-$C_{12}$ aryl group or $C_5$-$C_{12}$-aryl-$C_1$-$C_6$ alkyl group;

5) pyrazolium cation with the general formula

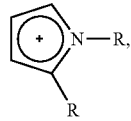

in which the pyrazole core may be substituted with at least one group selected from $C_1$-$C_6$ alkyl group, $C_1$-$C_6$ alkoxy group, $C_1$-$C_6$ hydroxyalkyl group, $C_1$-$C_6$ aminoalkyl group, $C_5$-$C_{12}$ aryl group or $C_5$-$C_{12}$-aryl-$C_1$-$C_6$ alkyl group; and 6) triazolium cation with the general formula

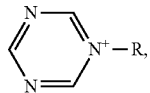

in which the triazole core may be substituted with at least one group selected from $C_1$-$C_6$ alkyl group, $C_1$-$C_6$ alkoxy group, $C_1$-$C_6$ hydroxyalkyl group, $C_1$-$C_6$ aminoalkyl group, $C_5$-$C_{12}$ aryl group or $C_5$-$C_{12}$-aryl-$C_1$-$C_6$ alkyl group; or 7) guanidinium cation with the general formula

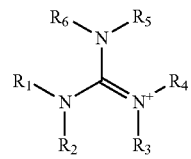

wherein and the radicals $R_1$, $R_2$, $R_3$, $R_4$, $R_5$, $R_6$ are selected independently at each occurrence from the group consisting of:
- linear or branched, saturated or unsaturated, aliphatic or alicyclic alkyl group with 1 to 20 carbon atoms;
- heteroaryl group, heteroaryl-$C_1$-$C_6$ alkyl group with 3 to 8 carbon atoms in the heteroaryl radical and at least one heteroatom selected from N, O and S which may be substituted with at least one group selected from $C_1$-$C_6$ alkyl group and/or halogen atoms;
- aryl, aryl-$C_1$-$C_6$ alkyl group with 5 to 12 carbon atoms in the aryl radical, which may optionally be substituted with at least one $C_1$-$C_6$ alkyl group and/or a halogen atom; and the radical R is selected from the group consisting of:
- linear or branched, saturated or unsaturated, aliphatic or alicyclic alkyl group with 1 to 20 carbon atoms;
- heteroaryl-$C_1$-$C_6$ alkyl group with 3 to 8 carbon atoms in the aryl radical and at least one heteroatom selected from N, O and S, which may be substituted with at least one $C_1$-$C_6$ alkyl group and/or halogen atom;
- aryl-$C_1$-$C_6$ alkyl group with 5 to 12 carbon atoms in the aryl radical, which may be substituted with at least one $C_1$-$C_6$ alkyl group and/or halogen atom;
- wherein any two of R, $R_1$, $R_2$, $R_3$, $R_4$, $R_5$, $R_6$ can join together to form a 4- to 8-membered heterocycle including the heteroatom to which each is attached.

In some embodiments, imidazolium cation is of the general formula

in which the imidazole core may be substituted with at least one group selected from $C_1$-$C_6$ alkyl group, $C_1$-$C_6$ alkoxy group, $C_1$-$C_6$ hydroxyalkyl group, $C_5$-$C_{12}$ aryl group or $C_5$-$C_{12}$-aryl-$C_1$-$C_6$ alkyl group.

In some embodiments, pyridinium cation is of the general formula

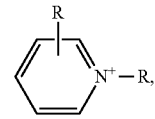

in which the pyridine core may be substituted with at least one group selected from $C_1$-$C_6$ alkyl group, $C_1$-$C_6$ alkoxy group, $C_1$-$C_6$ hydroxyalkyl group, $C_5$-$C_{12}$ aryl group or $C_5$-$C_{12}$-aryl-$C_1$-$C_6$ alkyl group.

In some embodiments, pyrazolium cation is of the general formula

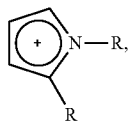

in which the pyrazole core may be substituted with at least one group selected from $C_1$-$C_6$ alkyl group, $C_1$-$C_6$ alkoxy group, $C_1$-$C_6$ hydroxyalkyl group, $C_5$-$C_{12}$ aryl group or $C_5$-$C_{12}$-aryl-$C_1$-$C_6$ alkyl group.

In some embodiments, triazolium cation is of the general formula

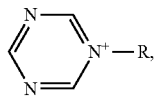

in which the triazole core may be substituted with at least one group selected from $C_1$-$C_6$ alkyl group, $C_1$-$C_6$ alkoxy group, $C_1$-$C_6$ hydroxyalkyl group, $C_5$-$C_{12}$ aryl group or $C_5$-$C_{12}$-aryl-$C_1$-$C_6$ alkyl group.

In some embodiments, imidazolium cation is of the general formula

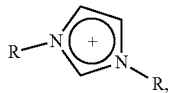

in which the imidazole core may be substituted with at least one group selected from $C_1$-$C_6$ alkyl group, $C_1$-$C_6$ alkoxy group, and $C_1$-$C_6$ hydroxyalkyl group.

In some embodiments, pyridinium cation is of the general formula

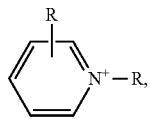

in which the pyridine core may be substituted with at least one group selected from $C_1$-$C_6$ alkyl group, $C_1$-$C_6$ alkoxy group, and $C_1$-$C_6$ hydroxyalkyl group.

In some embodiments, pyrazolium cation is of the general formula

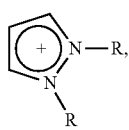

in which the pyrazole core may be substituted with at least one group selected from $C_1$-$C_6$ alkyl group, $C_1$-$C_6$ alkoxy group, and $C_1$-$C_6$ hydroxyalkyl group.

In some embodiments, triazolium cation is of the general formula

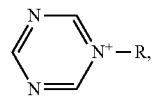

in which the triazole core may be substituted with at least one group selected from $C_1$-$C_6$ alkyl group, $C_1$-$C_6$ alkoxy group, and $C_1$-$C_6$ hydroxyalkyl group.

In some embodiments, the radicals $R_1$, $R_2$, $R_3$, $R_4$, $R_5$, $R_6$ are selected independently at each occurrence from the group consisting of:
  linear or branched, saturated or unsaturated, aliphatic or alicyclic alkyl groups with 1 to 20 carbon atoms, 1 to 15 carbon atoms, 2 to 18 carbon atoms, 3 to 18 carbon atoms, 4 to 18 carbon atoms, or 5 to 12 carbon atoms; and
  aryl, aryl-$C_1$-$C_6$ alkyl groups with 5 to 12 carbon atoms in the aryl radical, which may optionally be substituted with at least one $C_1$-$C_6$ alkyl group and/or at least one halogen atom.

In some embodiments, the radical R is selected from the group consisting of:
  linear or branched, saturated or unsaturated, aliphatic or alicyclic alkyl groups with 1 to 20 carbon atoms, 1 to 15 carbon atoms, 2 to 18 carbon atoms, 3 to 18 carbon atoms, 4 to 18 carbon atoms, or 5 to 12 carbon atoms; and
  aryl, aryl-$C_1$-$C_6$ alkyl groups with 5 to 12 carbon atoms in the aryl radical, which may optionally be substituted with at least one $C_1$-$C_6$ alkyl group and/or at least one halogen atom.

In some embodiments,

Exemplary quaternary ammonium cations include substituted or unsubstituted N1,N1-(di-(C1-C8 alkyl))-piperidinium, N1,N1-(di-(C1-C8 alkyl))-morpholinium, N1,N1-(di-(C1-C8 alkyl))-pyrrolidinium, tetralkylammonium, ethyl-dimethyl-propyl-ammonium, methyl-trioctylammonium, ethyl-dimethyl-(2-methoxyethyl)ammonium, 1,1-dimethylpyrrolidinium, 1-butyl-1-methylpyrrolidinium, 1-octyl-1-methylpyrrolidinium, 1-hexyl-1-methylpyrrolidinium, 1-(6-aminohexyl)-1-methylpyrrolidinium, 1-(2-methoxyethyl)-1-methylpyrrolidinium, tetramethylammonium, tetrabutylammonium, (2-hydroxyethyl)trimethylammonium, 1-(hydrazinocarbonylmethyl)-trimethylammonium, ethyl-dimethyl-(5-diisopropylamino-3-oxapentyl)ammonium, ethyl-dimethyl-cyanomethyl-ammonium, N-(2-methoxyethyl)-N-methyl-morpholinium, 1-(2-methoxyethyl)-1-methyl-piperidinium, 1-(2-methoxyethyl)-1-methyl-pyrrolidinium, 1-butyl-1-methylpyrrolidinium, 1-methyl-1-octyl-pyrrolidinium, 1-methyl-1-hexyl-pyrrolidinium, 1,1-dimethylpyrrolidinium, 1-(methoxyethyl)-1-methylpyrrolidinium, and others.

Exemplary imidazolium cations include substituted or unsubstituted N1-(C1-C8 alkyl)imidazolium, N1-(C1-C8 alkyl)-3-(C1-C8 alkyl)-imidazolium, 1-ethyl-3-methyl-imidazolium, 1,3-dimethyl-imidazolium, 1-propyl-3-methyl-imidazolium, 1-hexyl-3-methyl-imidazolium, 1-octyl-3-methyl-imidazolium, 1-cyanomethyl-3-methyl-imidazolium, 1-benzyl-3-methyl-imidazolium, 1-butyl-3-methyl-imidazolium, 1-butyl-2,3-dimethyl-imidazolium, 1-ethyl-2,3-dimethyl-imidazolium, 1-hexyl-2,3-dimethyl-imidazolium, 1,2,3-(trialkyl)imidazolium, 1,2,3-trimethyl-imidazolium, 1-ethyl-2,3-dimethyl-imidazolium, 1-propyl-2,3-dimethylimidazolium, 1-butyl-2,3-dimethyl-imidazolium, 1-hexyl-2,3-dimethyl-imidazolium, 1-(2-hydroxyethyl)-3-methylimidazolium, and others.

Exemplary phosphonium cations include substituted or unsubstituted peralkyl phosphonium, and trihexyl(tetradecyl)phosphonium, and others.

Exemplary pyridinium cations include substituted or unsubstituted N—(C1-C8 alkyl)-pyridinium, N-butyl-pyridinium, N-hexyl-pyridinium, N—(C1-C8 alkyl)-(C1-C8 alkyl)pyridinium, N—(C1-C8 alkyl)-(2-, 3- and/or 4-($C_1$-$C_8$ alkyl)-pyridinium, N-butyl-3-methyl-pyridinium, N-ethyl-3-methyl-pyridinium, N-butyl-4-methyl-pyridinium, N-hexyl-4-dimethylamino-pyridinium, N-ethyl-3-hydroxymethyl-pyridinium, N-(3-hydroxypropyl)-pyridinium, N-(3-hydroxypropyl)pyridinium, and others.

Exemplary pyrazolium cations include substituted or unsubstituted N1-(C1-C8 alkyl)-N2-(C1-C8 alkyl)pyrazolium, N1-(C1-C8 alkyl)-N2-(C1-C8 alkyl)-(3,4- and/or 5-(C1-C8 alkyl)-pyrazolium, and others.

Exemplary triazolium cations include substituted or unsubstituted N1-(C1-C8 alkyl)-triazolium, N1-(C1-C8 alkyl)-(2-, 4- and/or 6-(C1-C8 alkyl)-triazolium, and others.

Exemplary guanidinium cations include substituted or unsubstituted peralkylguanidinium, N1,N1-(di-C1-C8-alkyl)-N2,N2-(di-C1-C8-alkyl)-N3,N3-(di-C1-C8 alkyl) guanidinium, and others.

The cations disclosed herein are commercially available from sources such as Sigma-Aldrich (St. Louis, Mo.), 3M United Kingdom PLC (UK), Akzo Nobel N.V. (The Netherlands), BASF (Florham Park, N.J.), Ashland Chemical Company (Covington, Ky.), Rohm and Haas (Philadelphia, Pa.), Chemtura Corporation (Middlebury, Conn.), Merck KGaA (Darmstadt, Germany), EMD Chemicals Inc. (Gibbstown, N.J.), and other specialty chemical companies worldwide.

When the chiral anion is an anionic CD derivative, the anion can comprise one or more individual anionic CD derivative species differing in individual degree of substitution, such that the average degree of substitution (ADS) for the CD composition is calculated, as described herein, from the individual degrees of substitution (IDS) of the species. In some embodiments, the individual CD derivative species have the same substituent(s) but differ in the number of substituent(s) per cyclodextrin molecule. In some embodiments, the individual CD derivative species have different substituent(s) and differ in the number of substituent(s) per cyclodextrin molecule.

The cyclodextrin ring of the CD derivative can be derived from an α-, β-, or γ-parent cyclodextrin. A parent cyclodextrin includes a secondary hydroxyl group on the C-2 and C-3 positions of the glucopyranose residues forming the cyclodextrin and a primary hydroxyl on the C-6 position of the same. Each of these hydroxyl moieties is available for derivatization by substituent precursor. Depending upon the synthetic methodology employed, the substituent moieties may be distributed randomly or in a somewhat ordered manner among the available hydroxyl positions. The regioisomerism of derivatization of the CD derivative by the anionic functional group Z can be varied as desired such that a majority of the substituents present can be preferentially located at a primary hydroxyl group or at one or both of the secondary hydroxyl groups of the parent cyclodextrin. In some embodiments, a CD derivative molecule comprises a minority of the substituent moieties located at the C-6 position, and a majority of the substituent moieties is located at the C-2 and/or C-3 position. In other embodiments, the substituent moieties of a CD derivative molecule are substantially evenly distributed among the C-2, C-3 and C-6 positions. In some embodiments, the primary distribution of substituents is C3>C2>C6, while in other embodiments the primary distribution of substituents is C2>C3>C6. In some embodiments, the primary distribution of substituents is C6>C3>C2 or C6>C2>C3.

The CD derivative can include any amount of underivatized parent cyclodextrin that has been added thereto and/or that is present due to incomplete removal of the underivatized cyclodextrin during processing/preparation of the cyclodextrin derivative. In some embodiments, the CD derivative comprises less than 50% wt., less than 40% wt., less than 30% wt., less than 20% wt., less than 10% wt., less than 5% s wt., less than 1% wt., less than 0.5% wt. or less than 0.1% wt. of underivatized CD.

When the chiral salt of the invention comprises an anionic CD derivative and a compound, or mixture of compounds, of the Formula 1:

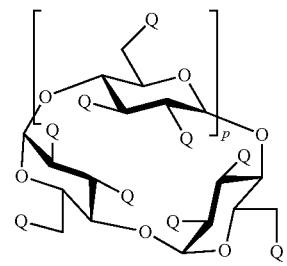

Formula I wherein:
p is 4, 5 or 6;
Q is independently selected at each occurrence from —OH, —SAET, —SFAET, —SNT-T, —SFT-T, —CAE-T, —SCN-T, —SATE-T, —CXT-T, —PAE-T, —PHT-T, and —PNT-T, wherein at least one Q is not —OH, and "A" in each of the above groups is independently selected upon each occurrence from an "alkyl" or "alkylene" group as defined herein; and T is independently selected at each occurrence from the cations (chiral and/or achiral cations) disclosed herein, wherein at least one T is a non-metal cation (such as a quaternary nitrogen-containing cation or a phosphonium cation) and at least one T is not —H.

In some embodiments, at least one Q is independently selected at each occurrence from —OH, —SAET, —SFAET, —SNT-T, —SFT-T, —CAE-T, —SCN-T, —SATE-T, —CXT-T, —PAE-T, —PHT-T, and —PNT-T, and at least one Q is selected from the group consisting of -AE and —HAE.

In some embodiments, —SAE is a —O—($C_2$-$C_6$ alkylene)-$SO_3^-$ group, wherein at least one SAE is independently a —O—($C_2$-$C_6$ alkylene)-$SO_3^-$ group, a —O—$(CH_2)_g$$SO_3^-$ group, wherein g is 1 to 18, 1 to 14, 1 to 12, 1 to 8, 2 to 6, or 2 to 4, (e.g. —$OCH_2CH_2CH_2SO_3^-$ or —$OCH_2CH_2CH_2CH_2SO_3$). The terms "alkylene" and "alkyl," as used herein (e.g., in the —O—($C_2$-$C_6$-alkylene) $SO_3^-$ group), include linear, cyclic, and branched, saturated and unsaturated (i.e., containing one double bond) divalent alkylene groups and monovalent alkyl groups, respectively.

A cyclodextrin (CD) derivative salt comprises a distribution of plural individual species, each species having an individual degree of substitution (IDS). The content of each of the cyclodextrin species in a particular composition can be quantified using capillary electrophoresis The method of analysis (capillary electrophoresis, for example, for charged CD derivatives) is sufficiently sensitive to distinguish between compositions having only 5% or more of individual CD derivative species.

In a single parent CD molecule, there are 3v+6 hydroxyl moieties available for derivatization. Where v=4 (α-CD), "y" the degree of substitution for the moiety can range in value from 1 to 18. Where v=5 (β-CD), "y" the degree of substitution for the moiety can range in value from 1 to 21. Where v=6 (γ-CD), "y" the degree of substitution for the moiety can range in value from 1 to 24. In general, "y" also ranges in value from 1 to 3v+g, where g ranges in value from 0 to 5. "y" may also range from 1 to 2v+g, or from 1 to 1v+g. The underivatized parent cyclodextrins α-CD, β-CD or γ-CDs are commercially available from WACKER BIOCHEM CORP. (Adrian, Mich.) and other sources.

Some embodiments of the invention include those wherein: 1) more than half of the hydroxyl moieties of the cyclodextrin derivative are derivatized; 2) half or less than half of the hydroxyl moieties of the cyclodextrin derivative are derivatized; 3) at least one eighth of the hydroxyl moieties of the cyclodextrin derivative are derivatized; 4) at least one fourth of the hydroxyl moieties of the cyclodextrin derivative are derivatized; 5) at least one third of the hydroxyl moieties of the cyclodextrin derivative are derivatized; 6) at least three eighths of the hydroxyl moieties of the cyclodextrin derivative are derivatized; 7) at least five eighths of the hydroxyl moieties of the cyclodextrin derivative are derivatized; 8) at least two thirds of the hydroxyl moieties of the cyclodextrin derivative are derivatized; 9) at least three quarters of the hydroxyl moieties of the cyclodextrin derivative are derivatized; 10) at least seven eighths of the hydroxyl moieties of the cyclodextrin derivative are derivatized; or 11) al of the hydroxyl moieties of the cyclodextrin derivative are derivatized.

Some embodiments of the invention include those wherein: 1) the substituents of the cyclodextrin derivative are the same upon each occurrence; 2) the substituents of the cyclodextrin derivative comprise at least two different substituents; or 3) the substituents of the cyclodextrin derivative comprise at least three different substituents.

The cyclodextrin derivatives can differ in their degree of substitution by functional groups, the number of carbons in the functional groups, their molecular weight, the number of glucopyranose units contained in the base cyclodextrin used to form the derivatized cyclodextrin and or their substitution patterns. In addition, the derivatization of a cyclodextrin with functional groups occurs in a controlled, although not exact manner. For this reason, the degree of substitution is actually a number representing the average number of functional groups per cyclodextrin (for example, SBE7-β-CD, has an average of 7 substitutions per cyclodextrin). Thus, it has an average degree of substitution (ADS) of about 7. Given the above, the molecular weight of a particular derivatized cyclodextrin composition may vary from batch to batch.

A CD derivative generally comprises a distribution of different CD derivative species or molecules. For example, a SAE-CD derivative composition generally comprises plural SAE-CD species each having a specific individual degree of substitution with regard to the SAE substituent. As a consequence, the average DS (ADS) for SAE of a SAE-CD derivative represents an average of the individual DS (IDS) values of the population of individual molecules in the composition. For example, a SAE5.2-CD comprises a distribution of plural SAEx-CD molecules, wherein x (the DS for SAE groups) might range from 1 to 10-11 for individual CD molecules; however, the population of SAE-CD molecules is such that the average value for x (the ADS for SAE groups) is 5.2.

The ADS for a CD derivative is calculated based upon the IDS according to the following formulas: $CA=PAC \times MT$; $IDS=(CA/SCA) \times 100$; $ADS=\text{Summation } (IDS \times \text{peak number})/100$, wherein CA=Corrected Area, PAC=Peak Area Count, MT=Migration Time, IDS=Individual Degree of Substitution, SCA=Summation of Corrected Area, ADS=Average Degree of Substitution. These values can be obtained using CE.

The cyclodextrin derivative can have a high to low ADS. In some embodiments, the ADS for the ranges from 1 to 17 for α-CD, 1-20 for β-CD or 1-23 for γ-CD. In some embodiments, the ADS for each type of substituent of an anionic CD derivative ranges from 1 to <5, about 5 to <9, about 9 to <12, about 12 to <15, about 15 to 23, about 15 to 20, about 15 to 17, about 2 to <8, about 8 to <13, about 13 to 17, at least 4 to about 20, at least 4 to about 17, at least 4 to about 12, at least 5 to about 15, at least 5 to about 12, or from about 4 to about 10. The range of ADS that can be also be 4.5 to 7.5, 5.5 to 7.5, or 6.0 to 7.1. The individual degree of substitution of the ionic CD derivative, in terms of the non-hydroxyl moiety, is understood to be at least one.

In a CD derivative having at least two different types of substituents, the ADS for the first type of substituent can be the same as or different than the ADS for the second type of substituent. Any combination of the various ADS ranges and values disclosed herein can be used for each substituent in a CD derivative.

By varying the molar ratios of butane sultone to CD and propylene oxide to CD, a HPm-SBEn-β-CD can be prepared, wherein m ranges from 1 to 9 and n ranges from 1 to 9 and the sum of m+n ranges from 2 to 17 or 2 to 15 or 2 to 12 or 2 to 10. (See Example 12)

The CD derivative can also have a wide or narrow "span", which is the number of individual DS species within a CD derivative composition. For example, a CD derivative comprising a single species of CD derivative having a single specified individual DS is said to have a span of one, and the individual DS of the CD derivative equals the ADS of its CD derivative composition. An electropherogram, for example, of a SAE-CD derivative with a span of one should have only one SAE-CD species with respect to DS. A CD derivative composition having a span of two comprises two individual CD derivative species differing in their individual DS, and its electropherogram, for example, would indicate two different CD derivative species differing in DS Likewise, the span of a CD derivative composition having a span of three comprises three individual CD derivative species differing in their individual DS. Since a combination composition of the invention can comprise two or more different CD derivative compositions, each having its own ADS, the span of the combination composition will be at least 4, meaning that each starting CD derivative composition has a span of at least two.

Within a given CD derivative composition, the substituents of the CD derivative(s) thereof can be the same. For example, SAE moieties can have the same type of alkylene (alkyl) radical upon each occurrence in a CD derivative composition. In such an embodiment, the alkylene radical in the SAE moiety might be ethyl, propyl, butyl, pentyl or hexyl in each occurrence in a CD derivative composition.

Within a given CD derivative composition, at least two of the substituents of the CD derivative(s) thereof can be different. For example, SAE moieties can have different types of alkylene (alkyl) radical upon each occurrence in a CD derivative composition. In such an embodiment, the alkylene radical in the SAE moiety might be ethyl, propyl, butyl, pentyl or hexyl in one occurrence of the CD derivative composition and a different alkylene radical (selected from the same group) in the other occurrence of the same CD derivative composition.

An anionic cyclodextrin derivative can be provided in different salt forms. Suitable cations are disclosed herein. The anionic CD derivative can include a single type of cation or a mixture of two, three, four, five or more different cations.

A cyclodextrin derivative salt composition is optionally processed to remove the major portion of the underivatized parent cyclodextrin or other contaminants.

The CD derivative salt composition can be prepared by direct derivatization of an underivatized parent α, β, or γ-cyclodextrin, by further derivatization of a previously prepared cyclodextrin derivative, and/or by ion exchange. Such methods of derivatization include alterations in the known sequence of chemical synthetic steps for the preparation of water soluble cyclodextrin derivatives. Suitable methods are described herein.

In general, an anionic CD derivative is prepared by a process comprising: mixing in an aqueous medium parent cyclodextrin with substituent precursor in the presence of an alkalizing agent, thereby forming an aqueous reaction milieu comprising the anionic CD derivative; conducting one or more separation and/or purification steps to remove one or more unwanted components from the aqueous milieu thereby forming a partially purified or purified aqueous solution comprising the anionic CD derivative; and optionally removing water from the solution to form a concentrated solution or a dry anionic CD derivative. The process can further comprise the optional step of degrading or removing excess substituent precursor, if any, present in the aqueous reaction milieu after formation of the CD derivative or after completion of the mixing step. The process can further comprise the optional step of quenching.

The CD derivative salt (the chiral salt) of the invention can be prepared by ion exchange or direct derivatization. For ion exchange, a metal salt of an anionic CD derivative and a halide salt (or other salt) of a cation of the invention are placed in liquid medium with mixing. The metal salt of the anionic CD derivative and halide salt of the cation will be at least slightly soluble in the liquid medium. The following general formula generally describes some exemplary embodiments of the ion exchange reaction.

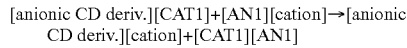

wherein [CAT1] is a metal cation, and [AN1] is a halide.

Ion exchange occurs between the salts to form a metal halide salt by-product ([CAT1][AN1]) and the ionic CD derivative salt of the invention ([anionic CD derive.][cation]), which can be separated by extraction, decantation, filtration, centrifugation as needed according to the properties of the liquid medium used. If the liquid medium is sufficiently hydrophobic, the metal halide salt can be made to precipitate. If a biphasic liquid medium is used, an organic phase and an aqueous phase can be used. The organic phase can be made to dissolve or extract the CD derivative salt and the aqueous phase can be made to dissolve or extract the metal halide salt. Alternatively, the CD derivative salt can be miscible with or soluble in the organic phase, and the metal halide salt can be substantially insoluble in the organic phase. Examples 1-10 detail exemplary ion exchange processes.

A CD derivative salt of the invention can also be made by direct derivatization of a CD in a solvent. An underivatized CD is placed in an organic solvent with an alkalizing agent (comprising an alkaline metal or alkaline earth metal), substituent precursor and halide salt of a cation. This process is essentially a combination process whereby derivatization and ion exchange are conducted simultaneously, sequentially or in an overlapping manner. As the anionic CD derivative is formed, it forms a salt complex with the cation to form the ionic liquid CD derivative and a metal halide salt by-product, which can be separated from the ionic liquid. Example 11 details an exemplary direct derivatization process.

The cyclodextrin derivative in the salt of the invention can have a monomodal, bimodal, trimodal or multi-modal substitution profile. These types of CD derivatives can be made according to PCT International Application No. PCT/US8/70969, which was filed Jul. 24, 2008 and the disclosure of which is hereby incorporated by reference.

Other materials that can be included in a composition of the invention include, among other things, one or more excipients and/or one or more active agents.

The invention also provides an active composition comprising an ionic liquid of the invention and one or more active agents, e.g. therapeutic agents. The active composition optionally further comprises one or more excipients. In some embodiments, the active agent, or a majority thereof, is complexed with the CD derivative composition. In other embodiments, the active agent, or a majority thereof, is not complexed with the CD derivative salt of the invention.

The ionic liquid composition of the invention can be used for substantially any known method or process wherein a CD derivative provides utility. The composition can be used for the same process or method that its starting CD derivative compositions are used. Suitable uses for a composition of the invention include use in pharmaceutical or non-pharmaceutical formulation. The composition of the invention can be used to solubilize, stabilize, taste-mask, suspend, immobilize, purify or extract one or more compounds formulated therewith. An active composition comprising an ionic liquid and one or more therapeutically effective agents can be used to treat (diagnose, prevent, cure, ameliorate, relieve, reduce the occurrence of, reduce the frequency of) a symptom, disease, or disorder that is therapeutically responsive to the one or more therapeutically effective agents.

The ionic liquid composition of the invention can be employed in compositions, formulations, methods and systems such as those disclosed in U.S. Pat. No. 5,134,127, U.S. Pat. No. 5,376,645, U.S. Pat. No. 6,046,177, U.S. Pat. No. 5,914,122, U.S. Pat. No. 5,874,418, U.S. Pat. No. 7,034,013, U.S. Pat. No. 6,869,939, and U.S. Pat. No. 6,133,248, and U.S. application Ser. No. 10/505,713, Ser. No. 11/076,072, Ser. No. 11/550,976, Ser. No. 11/109,303, Ser. No. 11/479,979, Ser. No. 11/613,187, Ser. No. 11/479,938, Ser. No. 11/855,642, Ser. No. 11/413,597, Ser. No. 11/479,937, No. 60/914,555, and No. 60/952,771, and PCT International Applications No. PCT/US05/38933, No. PCT/US06/62346, No. PCT/US07/71758, No. PCT/US07/71748, No. PCT/US07/72442, No. PCT/US07/72387, and No. PCT/US07/78465, the entire disclosures of which are hereby incorporated by reference. The ionic liquid of the invention can also be used as a suitable substitute for other known grades of similarly substituted cyclodextrin, particularly those known grades having lower purity, thereby resulting in compositions and formulations have greater stability, e.g. greater drug stability, e.g. U.S. Pat. No. 7,635,773 and U.S. Pat. No. 7,629,331.

The ionic liquid composition can also be used for the same processes and methods that other known ionic liquids are currently used for. However, the instant salts possess the advantage of being chiral and thus can be used to direct chiral conversions, reactions, extractions and other such processes.

A chiral salt of the invention can be used as a phase transfer catalyst. For example, the chiral salt can be used as a phase transfer catalyst for the acid or base catalyzed hydrolysis of a poorly water soluble ester. The ester and a sufficient amount of chiral salt of the invention (anionic cyclodextrin derivative with a cation as defined herein) are placed in a vessel containing an acidic or alkaline aqueous phase and an organic phase. The phases are mixed, optionally with heating or cooling, and optionally with pH adjustment to maintain the pH of the aqueous phase within a predetermined region. The chiral salt is present in an amount sufficient to dissolve a portion of the poorly water soluble ester in the aqueous phase. The ester is hydrolyzed. The unesterified compound can be recovered by acidification of the aqueous phase to a pH below the pKa of the acidic functional group of the unesterified compound and subsequent recovery by filtration of solidified unesterified compound or extraction of the unesterified compound into an organic phase. (See Example 16)

A chiral salt of the invention can be used as a chiral reaction medium. For example, the methods of Welton (1999, above), Wasserscheid (2000, above), Suarez et al. (1996 and 1997, above), and Chauvin et al. (1997, above) can be modified by employing the chiral salt of the invention instead of the ionic liquids disclosed therein. The methods of Takahashi et al. (J. Inclusion Phenomena and Macrocyclic Chemistry (1994), 17(1), 1-24), Szetli et al. (Cyclodextrin Technology, 1988, Kluwer Academic Publishers, The Netherlands), and Luo et al. (J. Org. Chem. (2009) 74(9), 3506-3515) can be modified by employing the chiral salt of the invention instead of the cyclodextrins disclosed therein.

A chiral salt of the invention can be used as a chiral extraction medium for selective or specific separation of an enantiomer from a racemic mixture or chirally enriched mixture of enantiomers, for selective or specific separation of a diastereomer from a mixture of stereoisomers, or for selective or specific separation of an epimer from a mixture of epimers or for selective or specific separation of one or more compounds from a group/mixture of structurally related compounds. For example, a biphasic mixture of the chiral salt and an organic solvent in which it is poorly or slightly miscible (less than 5% wt solubility) is formed. The organic solvent contains a mixture of enantiomers, diastereomers or epimers of a compound. For example, in a biphasic mixture, one of the enantiomers, stereoisomers or epimers is selectively or specifically complexed with the cyclodextrin ring of the chiral salt and brought into one phase leaving the other corresponding uncomplexed enantiomer, stereoisomer or epimer in the other phase. (See Example 18 for chiral selective extraction and Example 17 for compound selective extraction.)

A chiral salt of the invention can be used as an extraction medium in a supercritical fluid extraction process in order to separate one or more target compounds from a mass containing the one or more target compounds. The process employs a supercritical fluid and a chiral salt of the invention. The mass, comprising one or more target compounds, is treated with an ionic liquid and a supercritical fluid in a vessel and mixed. The supercritical fluid is formed by adjusting the atmospheric (temperature and pressure) conditions within the vessel to those that convert an extraction medium (solvent) into the supercritical fluid. The table below includes different solvents that can be used as the SCF extraction solvent and their corresponding critical temperature and critical pressure.

| Fluid | Critical Temperature (K) | Critical Pressure (bar) |
|---|---|---|
| Carbon dioxide | 304.1 | 73.8 |
| Ethane | 305.4 | 48.8 |
| Ethylene | 282.4 | 50.4 |
| Propane | 369.8 | 42.5 |
| Propylene | 364.9 | 46.0 |
| Trifluoromethane (Fluoroform) | 299.3 | 48.6 |
| Chlorotrifluoromethane | 302.0 | 38.7 |
| Trichlorofluoromethane | 471.2 | 44.1 |
| Ammonia | 405.5 | 113.5 |
| Water | 647.3 | 221.2 |
| Cyclohexane | 553.5 | 40.7 |
| n-Pentane | 469.7 | 33.7 |
| Toluene | 591.8 | 41.0 |

Carbon dioxide is a preferred supercritical fluid. Its critical temperature is 31.06° C., its critical pressure is 73.83 bar, and its critical density is 0.460 g/cm3. It is contemplated, however, that other compounds, or mixtures thereof, can be used in a SCF extraction.

In some embodiments, a co-solvent or modifier is included in the supercritical fluid. Modifiers generally possess volatility between that of the supercritical fluid and of the compound being extracted, and they must be miscible with the supercritical fluid. In some embodiments, the modifier is a liquid at ambient conditions. By way of example and without limitation, a modifier can be selected from the group consisting of ethanol, methanol, propanol, water, acetone, ethyl acetate, methylene chloride, etc. (See table above).

The mixture of ionic liquid, supercritical fluid and mass in the vessel is mixed. The supercritical fluid phase is then separated from the ionic liquid phase. The one or more target compounds are easily separated from the supercritical fluid phase by removal of the supercritical fluid, e.g. evaporation thereof. If there are one or more target compounds in the ionic liquid phase, they can be separated from the ionic liquid by treating it with an aqueous liquid, in which the ionic liquid is immiscible or only sparingly soluble, or with an organic liquid, in which the ionic liquid is immiscible or only sparingly soluble, such that the one or more compounds is extracted in the aqueous or organic liquid. Supercritical fluid extraction with ionic liquid and a supercritical fluid is especially useful when extracting useful compounds from plant materials, since plant masses contain many different compounds differing in hydrophilicity and lipophilicity. See Example 19.

A chiral salt of the invention can provide unexpected advantages over other compositions containing structurally related cyclodextrin derivative compositions. In regards to the CD derivative, by "structurally related" is meant, for example, that the substituent of the CD derivative in the composition is essentially the same as the substituent of CD derivative to which it is being compared but wherein the cation is different. Exemplary advantages may include an improved ability of the combination composition to stabilize a neutral, cationic or anionic molecule, such as an active agent, better than can the structurally related CD derivative composition.

A composition of the invention can be a liquid, solid, suspension, colloid, pellet, bead, granule, film, powder, gel, cream, ointment, paste, stick, tablet, capsule, osmotic device, dispersion, emulsion, patch or any other type of formulation.

As used herein, a "substituent precursor" means any agent or combination of agents and reaction conditions that result in the formation of an anionic substituent on a hydroxyl of a parent cyclodextrin. A substituent precursor can react with the oxygen atom of a hydroxyl moiety of a parent cyclodextrin thereby converting the hydroxyl moiety to a target moiety (substituent) on the cyclodextrin. In some embodiments, the substituent precursor is selected from the group consisting of sulfoalkylating agent, alkylating agent, alkenylating agent, hydroxyalkylating agent, hydroxalkenylating agent, esterifying agent, aminoalkylating agent, thioalkylating agent, carboxyalkylating agent, polymerizing agent, carbamating agent, carboxylating agent, carbonylating agent, oxidizing agent, glycosidating agent, sulfonating agent, halogenating agent, epoxyalkylating agent, and a combination thereof.

A substituent precursor can also be referred to herein as a sulfoalkylating agent. Exemplary sulfoalkylating agents that can be used to derivatize (etherify) the cyclodextrin include, by way of example and without limitation, alkyl sultone. Specific SAE (sulfoalkyl ether) precursors include 1,4-butane sultone, 1,5-pentane sultone, 1,3-propane sultone, and other sulfoalkylating agents.

Exemplary alkylating agents that can be used to derivatize (etherify) the cyclodextrin include, by way of example and without limitation, various alkyl sulfate esters. Specific AE (alkyl ether) precursors include sulfate esters such as diethyl sulfate, dimethyl sulfate, and dipropyl sulfate, or methylating agents such as trimethyloxonium tetrafluoroborate (TMOTFB), trimethyloxonium p-toluenesulfonate, trimethyloxonium hexafluorophosphate, trimethyloxonium hexafluoroantimonate, trimethyloxonium alkane/aryl sulfonate, dimethoxycarbenium tetrafluoroborate, and O-methyldibenzofuranium tetrafluoroborate, or trialkylsulfonium halide agents such as trimethylsulfonium iodide. Exemplary sulfoalkylating agents that can be used to derivatize (etherify) the cyclodextrin include, by way of example and without limitation, alkyl sultone. Specific SAE (sulfoalkyl ether) precursors include 1,4-butane sultone, 1,5-pentane sultone, 1,3-propane sultone, and other sulfoalkylating agents. Exemplary HAE (hydroxyalkyl ether) precursors that can be used to derivatize the cyclodextrin include 2,3-epoxy alcohols or halohydrins and others described in references cited herein. Exemplary HANE (hydroxyalkenyl ether) precursor that can be used to derivatize the cyclodextrin include 3,4-epoxy-1-butene, 4,5-epoxy-1-pentene, 5,6-epoxy-1-hexene and other epoxy alkenyl agents. Exemplary EPPE (epoxyalkyl ether; epoxyalkylating agent) precursor includes epichlorohydrin.

The anionic CD derivative in the salt of the invention can possess a pre-determined degree of substitution.

The phrase "alkali metal hydroxide" as used herein generally means lithium hydroxide, sodium hydroxide, or potassium hydroxide. If it is desired to produce a product suitable for parenteral administration, sodium hydroxide can be used.

Purification steps can employed, including the use of precipitation, diafiltration, dialysis, extraction, treatment with carbon or other solid medium, and/or ultrafiltration to remove by-products, e.g. metal halide salts, degraded substituent precursor, low molecular weight components, underivatized parent CD, and/or unreacted substituent precursor, from the CD derivative salt of the invention. Exemplary unwanted components (by-products) can include one or more of: low molecular weight impurities, salt, hydrolyzed sulfoalkylating agent, 5-(hydroxymethyl)-2-furaldehyde, unreacted β-CD, unreacted sulfoalkylating agent (1,4-butane sultone), degraded unreacted CD, degraded SAE-CD, other components, and combinations thereof.

Ultrafiltration, well known in the chemical arts, is a process in which a material is contacted with a semipermeable ultrafiltration membrane that passes low molecular weight impurities through the membrane. The molecular weight of the impurities passed through the membrane depends on the molecular weight cutoff for the membrane. For the instant invention a membrane having a molecular weight cutoff of 1,000 is typically employed. The desired product which is in the retentate is typically further treated with carbon powder to remove colors and further reduce any remaining impurities.

The filtration medium can be nylon, Teflon, PVDF or other compatible material. The pore size of the filtration can be varied as needed according to the particle size or molecular weight of species being separated from the CD derivative in a solution containing the same. The diafiltration and ultrafiltration steps can be conducted with filtration membranes having a 500 to 2000 Dalton, 500 to 1500 Dalton, 750 to 1250 Dalton, or 900 to 1100 Dalton, or about 1000 Dalton molecular weight cut-off.

For example, a reaction solution is diluted with aqueous solution and subjected to diafiltration during which the volume of the retentate is kept substantially constant. The diafiltration can be conducted over a 1000 Dalton filter such that one or more unwanted components pass through the filter but the majority of the anionic CD derivative is retained in the retentate rather than passing through with the filtrate. The ultrafiltration is then conducted by allowing the volume of the retentate to decrease thereby concentrating the retentate. A 1000 Dalton filter can also be used for the ultrafiltraton. The retentate comprises the anionic CD derivative and can then be optionally treated with activated carbon or otherwise purified.

Among other uses, a water soluble cyclodextrin derivative can be used to solubilize and/or stabilize a wide range of different materials and to prepare formulations for particular applications. The present cyclodextrin derivative may provide enhanced solubility and/or enhanced chemical, thermochemical, hydrolytic and/or photochemical stability of other ingredients in a composition. For example, a SAE-CD may be used to stabilize an active agent in an aqueous medium. A CD derivative composition may also be used to increase the solubility of an active agent in an aqueous medium. For example, an increase in the binding constant for a particular active agent is observed upon conversion of a CD derivative composition to a combination composition.

As used herein, the term non-covalent ionic bond refers to a bond formed between an anionic species and a cationic species. The bond is non-covalent such that the two species together form a salt or ion pair. An anionic derivatized cyclodextrin provides the anionic species of the ion pair and the [cation] of the invention provides the cationic species of the ion pair. Since an anionic derivatized cyclodextrin is multivalent, it will comprise plural [cations], approximating at least one cations for each anionic substituent. Where the anionic substituent is divalent, the anionic CD derivative can comprise one or two cations per anionic substituent.

By virtue of the strong salt binding complex between the cation and anion in the ionic liquid of the invention, due to Bronsted acid and base binding, the ionic salt of the invention advantageously remains complexed in its initial salt form even in the presence of weaker bases. For example, the very strong Bronsted property of the quaternary nitrogen-containing cation generally ensures that the same cation remain preferentially salt-complexed (ion pair) with the anionic cyclodextrin derivative even when the ionic liquid is exposed to a primary amine or even a secondary amine. This advantage makes the ionic liquid of the invention more advantageous than other salt forms of anionic cyclodextrin derivatives.

The composition of the invention can include one or more active agents. The active agent included in the present invention can possess a wide range of values for water solubility, bioavailability and hydrophilicity. Active agents to which the present invention is particularly suitable include water insoluble, poorly water soluble, slightly water soluble, moderately water soluble, water soluble, very water soluble, hydrophobic, or hydrophilic therapeutic agents. It will be understood by the artisan of ordinary skill that an active agent used in the formulation of the present invention is independently selected at each occurrence from any known active agent and from those disclosed herein. It is not necessary that the active agent complex with the derivatized cyclodextrin or form an ionic association with the derivatized cyclodextrin.

Active agents generally include physiologically or pharmacologically active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents, pharmaceutically effective active agents, and other such compounds for pharmaceutical, veterinary, horticultural, household, food, culinary, agricultural, cosmetic, industrial, cleaning, confectionery and flavoring applications. The active agent can be present in its neutral, ionic, salt, basic, acidic, natural, synthetic, diastereomeric, isomeric, enantiomerically pure, racemic, hydrate, chelate, derivative, analog, or other common form.

Representative pharmaceutically effective active agents include nutrients and nutritional agents, hematological agents, endocrine and metabolic agents, cardiovascular agents, renal and genitourinary agents, respiratory agents, central nervous system agents, gastrointestinal agents, anti-infective agents, biologic and immunological agents, dermatological agents, ophthalmic agents, antineoplastic agents, and diagnostic agents. Exemplary nutrients and nutritional agents include as minerals, trace elements, amino acids, lipotropic agents, enzymes and chelating agents. Exemplary hematological agents include hematopoietic agents, antiplatelet agents, anticoagulants, coumarin and indandione derivatives, coagulants, thrombolytic agents, antisickling agents, hemorrheologic agents, antihemophilic agents, hemostatics, plasma expanders and hemin. Exemplary endocrine and metabolic agents include sex hormones, uterine-active agents, bisphosphonates, antidiabetic agents, glucose elevating agents, adrenocortical steroids, parathyroid hormone, thyroid drugs, growth hormones, posterior pituitary hormones, octreotide acetate, imiglucerase, calcitonin-salmon, sodium phenylbutyrate, betaine anhydrous, cysteamine bitartrate, sodium benzoate and sodium phenylacetate, bromocriptine mesylate, cabergoline, agents for gout, and antidotes. Antifunal agents including, but not limited to Posaconazole, Voriconazole, Clotrimazole, Ketoconazole, Oxiconazole, Sertaconazole, Tetconazole, Fluconazole, Itraconazole and Miconazole. Antipsychotic agents including, but not limited to clozapine, prochlorperazine, haloperidol, thioridazine, thiothixene, risperidone, trifluoperazine hydrochloride, chlorpromazine, Aripiprazole, loxapine, Loxitane, Zyprexa, Seroquel, Resperidal and ziprasidone Exemplary cardiovascular agents include nootropic agents, antiarrhythmic agents, calcium channel blocking agents, vasodilators, antiadrenergics/sympatholytics, renin angiotensin system antagonists, antihypertensive agent combinations, agents for pheochromocytoma, agents for hypertensive emergencies, antihyperlipidemic agents, antihyperlipidemic combination products, vasopressors used in shock, potassium removing resins, edetate disodium, cardioplegic solutions, agents for patent ductus arteriosus, and sclerosing agents. Exemplary renal and genitourinary agents include interstitial cystitis agents, cellulose sodium phosphate, anti-impotence agents, acetohydroxamic acid (aha), genitourinary irrigants, cystine-depleting agents, urinary alkalinizers, urinary acidifiers, anticholinergics, urinary cholinergics, polymeric phosphate binders, vaginal preparations, and diuretics. Exemplary respiratory agents include bronchodilators, leukotriene receptor antagonists, leukotriene formation inhibitors, respiratory inhalant products, nasal decongestants, respiratory enzymes, lung surfactants, antihistamines, normarcotic antitussives, and expectorants. Exemplary central nervous system agents include CNS stimulants, narcotic agonist analgesics, narcotic agonist-antagonist analgesics, central analgesics, acetaminophen, salicylates, normarcotic analgesics, nonsteroidal anti-inflammatory agents, agents for migraine, antiemetic/antivertigo agents, antianxiety agents, antidepressants, antipsychotic agents, cholinesterase inhibitors, nonbarbiturate sedatives and hypnotics, nonprescription sleep aids, barbiturate sedatives and hypnotics, general anesthetics, injectable local anesthetics, anticonvulsants, muscle relaxants, antiparkinson agents, adenosine phosphate, cholinergic muscle stimulants, disulfuram, smoking deterrents, riluzole, hyaluronic acid derivatives, and botulinum toxins. Exemplary gastrointestinal agents including $H\,pylori$ agents, histamine H2 antagonists, proton pump inhibitors, sucralfate, prostaglandins, antacids, gastrointestinal anticholinergics/antispasmodics, mesalamine, olsalazine sodium, balsalazide disodium, sulfasalazine, celecoxib, infliximab, tegaserod maleate, laxatives, antidiarrheals, antiflatulents, lipase inhibitors, GI stimulants, digestive enzymes, gastric acidifiers, hydrocholeretics, gallstone solubilizing agents, mouth and throat products, systemic deodorizers, and anorectal preparations. Exemplary anti-infective agents including penicillins, cephalosporins and related antibiotics, carbapenem, monobactams, chloramphenicol, quinolones, fluoroquinolones, tetracyclines, macrolides, spectinomycin, streptogramins, vancomycin, oxalodinones, lincosamides, oral and parenteral aminoglycosides, colistimethate sodium, polymyxin b sulfate, bacitracin, metronidazole, sulfonamides, nitrofurans, methenamines, folate antagonists, antifungal agents, antimalarial preparations, antituberculosis agents, amebicides, antiviral agents, antiretroviral agents, leprostatics, antiprotozoals, anthelmintics, and cdc anti-infective agents. Exemplary biologic and immunological agents including immune globulins, monoclonal antibody agents, antivenins, agents for active immunization, allergenic extracts, immunologic agents, and antirheumatic agents. Exemplary dermatological agents includw topical antihistamine preparations, topical anti-infectives, anti-inflammatory agents, anti-psoriatic agents, antiseborrheic products, arnica, astringents, cleansers, capsaicin, destructive agents, drying agents, enzyme preparations, topical immunomodulators, keratolytic agents, liver derivative complex, topical local anesthetics, minoxidil, eflornithine HCl, photochemotherapy agents, pigment agents, topical poison ivy products, topical pyrimidine antagonist, pyrithione zinc, retinoids, rexinoids, scabicides/pediculicides, wound healing agents, emollients, protectants, sunscreens, ointment and lotion bases, rubs and liniments, dressings and granules, and physiological irrigating solutions. Exemplary ophthalmic agents include agents for glaucoma, mast cell stabilizers, ophthalmic antiseptics, ophthalmic phototherapy agents, ocular lubricants, artificial tears, ophthalmic hyperosmolar preparations, and contact lens products. Exemplary antineoplastic agents include alkylating agents, antimetabolites, antimitotic agents, epipodophyllotoxins, antibiotics, hormones, enzymes, radiopharmaceuticals, platinum coordination complex, anthracenedione, substituted ureas, methylhydrazine derivatives, imidazotetrazine derivatives, cytoprotective agents, dna topoisomerase inhibitors, biological response modifiers, retinoids, rexinoids, monoclonal antibodies, protein-tyrosine kinase inhibitors, porfimer sodium, mitotane (o, p'-ddd), and arsenic trioxide. Exemplary diagnostic agents include in vivo diagnostic aids, in vivo diagnostic biologicals, and radiopaque agents.

The above-mentioned list should not be considered exhaustive and is merely exemplary of the many embodiments considered within the scope of the invention. Many other active agents can be administered with the formulation of the present invention.

An active agent contained within a formulation of the invention can be present as its pharmaceutically acceptable salt. As used herein, "pharmaceutically acceptable salt" refers to derivatives of the disclosed compounds wherein the active agent is modified by reacting it with an acid or base as needed to form an ionically bound pair. Suitable salts are found in *Remington's Pharmaceutical Sciences*, $17^{th}$. ed., Mack Publishing Company, Easton, Pa., 1985, the relevant disclosure of which is hereby incorporated by reference.

A liquid vehicle included in a composition of the invention comprises an aqueous liquid carrier, such as water, aqueous alcohol, or aqueous organic solvent, or a non-aqueous liquid carrier.

An organic solvent used herein can be a non-polar organic solvent, moderately polar organic solvent or polar organic solvent. A non-polar organic solvent includes, for example, toluene, saturate alkane, cyclohexane, cyclopentane, xylene, hexane, octane, pentane, butane, heptane, nonane, benzene, carbon tetrachloride, turpentine, mineral spirits, petroleum ether and others known to those of ordinary skill in the art. A moderately polar organic solvent includes, for example, methylene chloride, diethyl ether, tetrahydrofuran, ethyl acetate, butanol, t-butyl methyl ether, butyl acetate, methoxy ethylacetate, t-butyl alcohol and others known to those of ordinary skill in the art. A polar organic solvent includes, for example, methyl ethyl ketone, acetonitrile, 2-methoxyethanol, 2-ethoxyethyl ether, acetone, dimethylformamide, dimethylacetamide, diethyl ketone, dioxane, N-methylpyrrolidone dimethylsulfoxide, propanol, ethanol, methanol, pyridine, glyme, diglyme and others known to those of ordinary skill in the art.

Exemplary organic solvents also include, by way of example, ethanol, glycerin, polyethylene glycols, propylene glycol, poloxomers, tetrahydrofuran, methanol, propanol, iso-propanol, methyl ethyl ketone, acetone, dioxane, chloroform, methylene chloride, ethyl acetate, methylacetate, propyl acetate, butyl acetate, diethylene glycol, glyme, diglyme, dimethyl ether, heptane, methyl t-butyl ether, pentane, petroleum ether, xylene, actonitrile, dimethylormamide, dimethylacetamide, dimethylsulfoxide, N-methylpyrrolidone, butanol, diethyl ether, hexane, toluene, mineral spirits, and others known to those of ordinary skill in the art.

Although not necessary, the salt of the present invention can be included in a formulation which further comprises one or more excipients selected from the group consisting of a conventional preservative, antifoaming agent, antioxidant, buffering agent, acidifying agent, alkalizing agent, bulking agent, colorant, complexation-enhancing agent, cryoprotectant, hydrophilic polymer, electrolyte, glucose, emulsifying agent, oil, plasticizer, solubility-enhancing agent, organic solvent, stabilizer, tonicity modifier, flavors, sweeteners, adsorbents, antiadherent, binder, diluent, direct compression excipient, disintegrant, glidant, lubricant, opaquant, polishing agent, complexing agents, fragrances, other excipients known by those of ordinary skill in the art for use in formulations, and a combination thereof.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, lithium hydroxide, potassium hydroxide, sodium borate, sodium carbonate, sodium bicarbonate, sodium hydroxide, triethanolamine, diethanolamine, organic amine base, alkaline amino acids, alkali metal hydroxide, transition metal hydroxide, transition metal oxide, magnesium oxide, magnesium hydroxide, calcium oxide, calcium hydroxide, manganese oxide, manganese hydroxide, alkali metal bicarbonate, transition metal bicarbonate, alkali metal borate, transition metal borate, alkali metal hydride, transition metal hydride, others known to those of ordinary skill in the art, or a combination thereof and.

As used herein, the term "acidifying agent" is intended to mean a compound used to provide an acidic medium for product stability. Such compounds include, by way of example and without limitation, acetic acid, acidic amino acids, citric acid, fumaric acid and other alpha hydroxy acids, hydrochloric acid, ascorbic acid, phosphoric acid, sulfuric acid, tartaric acid and nitric acid and others known to those of ordinary skill in the art.

As used herein, the term "complexing agent" refers to compounds that form a non-covalent complex with a compound in solution. Exemplary complexing agents include chiral tartaric acid, chiral tartaric ester, zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates, layered silicates, calcium ion, barium ion, titanium ions, zinc ion, aluminum ions, sulfur ions, silicaceous ions salt of mineral and organic acid, water soluble tetraethylsulftonate derivative of 2-methylresorcinarene, and others known to those of ordinary skill in the art. For the purposes herein, a complexing agent excludes an anionic cyclodextrin derivative of the invention.

Hydrophilic polymers can be used as complexation-enhancing, solubility-enhancing and/or water activity reducing agents to improve the performance of formulations containing a cyclodextrin-based preservative. Loftsson has disclosed a number of polymers suitable for combined use with a cyclodextrin (underivatized or derivatized) to enhance the performance and/or properties of the cyclodextrin. Suitable polymers are disclosed in *Pharmazie* (2001), 56(9), 746-747; *International Journal of Pharmaceutics* (2001), 212(1), 29-40; Cyclodextrin: From Basic Research to Market, International Cyclodextrin Symposium, 10th, Ann Arbor, Mich., United States, May 21-24, 2000 (2000), 10-15 (Wacker Biochem Corp.: Adrian, Mich.); PCT International Publication No. WO 9942111; *Pharmazie*, 53(11), 733-740 (1998); *Pharm. Technol. Eur.*, 9(5), 26-34 (1997); *J. Pharm. Sci.* 85(10), 1017-1025 (1996); European Patent Application EP0579435; Proceedings of the International Symposium on Cyclodextrins, 9th, Santiago de Comostela, Spain, May 31-Jun. 3, 1998 (1999), 261-264 (Editor(s): Labandeira, J. J. Tones; Vila-Jato, J. L. Kluwer Academic Publishers, Dordrecht, Neth); *S.T.P. Pharma Sciences* (1999), 9(3), 237-242; ACS Symposium Series (1999), 737(Polysaccharide Applications), 24-45; *Pharmaceutical Research* (1998), 15(11), 1696-1701; *Drug Development and Industrial Pharmacy* (1998), 24(4), 365-370; *International Journal of Pharmaceutics* (1998), 163(1-2), 115-121; Book of Abstracts, 216th ACS National Meeting, Boston, August 23-27 (1998), CELL-016, American Chemical Society; *Journal of Controlled Release*, (1997), 44/1 (95-99); *Pharm. Res.* (1997) 14(11), S203; *Investigative Ophthalmology & Visual Science*, (1996), 37(6), 1199-1203; Proceedings of the International Symposium on Controlled Release of Bioactive Materials (1996), 23rd, 453-454; *Drug Development and Industrial Pharmacy* (1996), 22(5), 401-405; Proceedings of the International Symposium on Cyclodextrins, 8th, Budapest, March 31-April 2, (1996), 373-376. (Editor(s): Szejtli, J.; Szente, L. Kluwer: Dordrecht, Neth.); *Pharmaceutical Sciences* (1996), 2(6), 277-279; *European Journal of Pharmaceutical Sciences*, (1996) 4(SUPPL.), S144; Third European Congress of Pharmaceutical Sciences Edinburgh, Scotland, UK Sep. 15-17, 1996; *Pharmazie*, (1996), 51(1), 39-42; *Eur. J. Pharm. Sci.* (1996), 4(Suppl.), S143; U.S. Pat. No. 5,472,954 and U.S. Pat. No. 5,324,718; *International Journal of Pharmaceutics* (Netherlands), (Dec. 29, 1995) 126, 73-78; Abstracts of Papers of the American Chemical Society, (2 Apr. 1995) 209(1), 33-CELL; *European Journal of Pharmaceutical Sciences*, (1994) 2, 297-301; *Pharmaceutical Research* (New York), (1994) 11(10), S225; *International Journal of Pharmaceutics* (Netherlands), (Apr. 11, 1994) 104, 181-184; and *International Journal of Pharmaceutics* (1994), 110(2), 169-77, the entire disclosures of which are hereby incorporated by reference.

Other suitable polymers are well-known excipients commonly used in the field of pharmaceutical formulations and are included in, for example, *Remington's Pharmaceutical Sciences*, 18th Edition, Alfonso R. Gennaro (editor), Mack Publishing Company, Easton, Pa., 1990, pp. 291-294; Alfred Martin, James Swarbrick and Arthur Commarata, *Physical Pharmacy. Physical Chemical Principles in Pharmaceutical Sciences*, 3rd edition (Lea & Febinger, Philadelphia, Pa., 1983, pp. 592-638); A. T. Florence and D. Altwood, (*Physicochemical Principles of Pharmacy, 2nd Edition*, MacMillan Press, London, 1988, pp. 281-334. The entire disclosures of the references cited herein are hereby incorporated by references. Still other suitable polymers include water-soluble natural polymers, water-soluble semi-synthetic polymers (such as the water-soluble derivatives of cellulose) and water-soluble synthetic polymers. The natural polymers include polysaccharides such as inulin, pectin, algin derivatives (e.g. sodium alginate) and agar, and polypeptides such as casein and gelatin. The semi-synthetic polymers include cellulose derivatives such as methylcellulose, hydroxyethylcellulose, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer). Other natural, semi-synthetic and synthetic polymers not named here which meet the criteria of water solubility, pharmaceutical acceptability and pharmacological inactivity are likewise considered to be within the ambit of the present invention.

A solubility-enhancing agent can be added to the formulation of the invention. A solubility-enhancing agent is a compound, or compounds, that enhance(s) the solubility of the active agent when in a liquid formulation. When such an agent is present, the ratio of cyclodextrin/active agent can be changed. Suitable solubility enhancing agents include one or more organic solvents, detergents, soaps, surfactant and other organic compounds typically used in parenteral formulations to enhance the solubility of a particular agent.

It should be understood, that compounds used in the chemicals arts generally can serve a variety of functions or purposes. Thus, if a compound named herein is mentioned only once or is used to define more than one term herein, its purpose or function should not be construed as being limited solely to that named purpose(s) or function(s).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The CD derivative salt of the invention can be present in exemplary forms such as a reconstitutable solid, tablet, capsule, pill, troche, patch, osmotic device, stick, suppository, implant, gum, effervescent composition, injectable liquid, powder, or solution.

In view of the above description and the examples below, one of ordinary skill in the art will be able to practice the invention as claimed without undue experimentation. The foregoing will be better understood with reference to the following examples that detail certain procedures for the preparation of molecules, compositions and formulations according to the present invention. All references made to these examples are for the purposes of illustration. The following examples should not be considered exhaustive, but merely illustrative of only a few of the many embodiments contemplated by the present invention.

Example 1

Preparation of SBE-β-CD 1,3-dialkyl-3-hydroxyalkylpyrazolium salt or SBE-β-CD 1,3-dialkyl-4-hydroxyalkylpyrazolium salt 1,3-dialkyl-4-hydroxyalkylpyrazolium halide (or 1,3-dialkyl-3-hydroxyalkyl-pyrazolium halide) and metal salt of sulfoalkyl ether β-CD (SBE-β-CD) are dissolved in water and optionally heated. The moles of pyrazolium halide approximates the average degree of substitution of the SBE-β-CD, meaning that for every mole of SBE-β-CD used, that number of moles times the ADS is the approximate number of moles of pyrazolium halide used. The water is slowly removed under vacuum. Water immiscible or water miscible organic solvent is added to the milieu. Any solid formed (typically the metal halide salt) is filtered off. The filtrate (comprising the SBE-β-CD pyrazolium salt) can be washed with water, water miscible organic solvent or water immiscible organic solvent. The organic phase is optionally dried. Concentrating and drying under a high vacuum yields the product: SBE-β-CD 1,3-dialkyl-4-hydroxyalkylpyrazolium salt or SBE-β-CD 1,3-dialkyl-3-hydroxyalkylpyrazolium salt.

Example 2

Preparation of SPE-γ-CD 1,3-dialkylimidazolium salt 1,3-dialkylimidazolium halide and metal salt of sulfoalkyl ether γ-CD (SPE-γ-CD) are dissolved in water and optionally heated. The moles or imidazolium halide (or carbonate) approximates the ADS of the SPE-γ-CD, meaning that for every mole of SPE-γ-CD used, that number of moles times the ADS is the approximate number of moles of 1,3-dialkylimidazolium halide (or carbonate) used. The water is slowly removed under vacuum. Water immiscible or water miscible organic solvent is added to the milieu. Any solid formed (typically the metal halide (or carbonate) salt) is filtered off. The filtrate (comprising the SPE-γ-CD imidazolium salt) can be washed with water, water miscible organic solvent or water immiscible organic solvent. The organic phase is optionally dried. Concentrating and drying under a high vacuum yields the product: SPE-γ-CD 1,3-dialkylimidazolium salt.

Example 3

Preparation of SPE-γ-CD 1,3-dimethylimidazolium salt

To an aqueous solution of SPE8-γ-CD (sulfopropyl ether γ-CD having an ADS of about 8) is added portionwise 1,3-dimethylimidazolium halide (MMIM HL) in ethanol. The moles of MMIM HL added approximates the average degree of substitution of the CD, meaning that for every mole of SPE-γ-CD used, that number of moles times 8 (the ADS of the SPE-γ-CD) is the approximate number of 1,3-dimethylimidazolium halide used. The batch is stirred for several hours optionally with heating. Water immiscible organic solvent is added to the milieu and mixed. Any solid formed (typically the metal halide salt) is filtered off. If no solid is form, the content of organic solvent is increased until an aqueous phase separates from the organic phase. The aqueous phase is discarded, optionally after further extraction with organic solvent. The organic phase (comprising the SPE8-γ-CD 1,3-dimethylimidazolium salt) can be washed with water, water miscible organic solvent or water immiscible organic solvent. The organic phase is optionally dried. Concentrating and drying under a high vacuum yields the product: SPE8-γ-CD 1,3-dimethylimidazolium salt.

Example 4

Preparation of CAE-CD 1-alkyl-3-alkylimidazolium salt

Method A.

To an ethanolic suspension of CAE7-α-CD metal salt (carboxyalkyl ether α-CD having an ADS of about 7) is added portionwise 1-alkyl-3-alkylimidazolium carbonate in ethanol. The moles of imidazolium added approximates the average degree of substitution of the CD, meaning that for every mole of CAE-α-CD used, that number of moles times 7 (the ADS of the CAE-α-CD) is the approximate number of moles of imidazolium carbonate used.

The batch is stirred for one day. Water immiscible organic solvent is optionally added to the milieu and mixed. Any solid formed (typically the metal carbonate salt) is filtered off and the filtrate is concentrated then washed with minimal amounts of water. The organic phase is optionally dried. Concentrating and drying under vacuum yields the product: CAE7-α-CD 1-alkyl-3-alkylimidazolium salt.

Method B.

To an aqueous solution of CAE5-β-CD metal salt (carboxyalkyl ether β-CD having an ADS of about 5) is added portionwise 1-alkyl-3-alkylimidazolium acetate in ethanol. The moles of imidazolium added approximates the average degree of substitution of the CD, meaning that for every mole of CAE-β-CD used, that number of moles times 5 (the ADS of the CAE-β-CD) is the approximate number of imidazolium acetate used. The batch is stirred for one day. Water immiscible organic solvent is added to the milieu and mixed. The aqueous phase is removed and optionally washed with water immiscible organic solvent. The organic phase(s) is optionally dried. Concentrating and drying under vacuum yields the product: CAE5-β-CD 1-alkyl-3-alkylimidazolium salt.

Example 5

Preparation of SAE-AE-CD 1,3-dialkyl-(2- or 4-hydroxyalkyl)imidazolium salt

To an aqueous solution of SAE7-AE5-β-CD metal salt (sulfoalkyl ether-alkyl ether β-CD having an ADS of about 7 for the SAE group and of about 5 for the AE group) is added 1,3-dialkyl-(2- or 4-hydroxyalkyl)imidazolium halide in tetrahydrofuran. The moles of imidazolium added approximates the ADS of the SAE group of the CD, meaning that for every mole of SAE7-AE5-β-CD used, that number of moles times 7 (the ADS of the SAE groups) is the approximate number of moles of imidazolium halide used. The batch is stirred for one day. Water immiscible organic solvent is added to the milieu and mixed. The aqueous phase is removed and optionally washed with water immiscible organic solvent. The organic phase(s) is optionally dried. Concentrating and drying under vacuum yields the product: SAE7-AE5-β-CD 1,3-dialkyl-(2- or 4-hydroxyalkyl)imidazolium salt.

Example 6

Preparation of SAE-HAE-CD 1-alkyl-(2-, 3- or 4-hydroxyalkyl)pyridinium salt

To an aqueous solution of SAE8-HAE5-β-CD metal salt (sulfoalkyl ether-alkyl ether β-CD having an ADS of about 8 for the SAE group and of about 5 for the HAE group) is added 1-alkyl-(2-, 3- or 4-hydroxyalkyl)pyridinium halide in acetonitrile. The moles of pyridinium added approximates the ADS of the SAE group of the CD, meaning that for every mole of SAE8-HAE5-β-CD used, that number of moles times 8 (the ADS of the SAE groups) is the approximate number of moles of pyridinium halide used. The batch is stirred for overnight. Water immiscible organic solvent is added to the milieu and mixed. The aqueous phase is removed and optionally washed with water immiscible organic solvent. The organic phase(s) is optionally dried. Concentrating and drying under vacuum yields the product: SAE8-HAE5-β-CD 1-alkyl-(2-, 3- or 4-hydroxyalkyl)pyridinium salt.

Example 7

Preparation of CAE-AE-CD 1-alkyl-4-hydroxyalkyltriazolium halide (or 1-alkyl-2-hydroxyalkyltriazolium halide) salt To an aqueous solution of CAE5-HAE8-γ-CD metal salt (carboxyalkyl ether-alkyl ether γ-CD having an ADS of about 5 for the CAE group and of about 8 for the HAE group) is added 1-alkyl-4-hydroxyalkyltriazolium carbonate (or 1-alkyl-2-hydroxyalkyltriazolium carbonate) in dioxane. The moles of triazolium added approximates the ADS of the CAE group of the CD, meaning that for every mole of CAE5-HAE8-γ-CD used, that number of moles times 5 (the ADS of the CAE groups) is the approximate number of moles of triazolium halide used. The batch is stirred for overnight. Water immiscible organic solvent is added to the milieu and mixed. The aqueous phase is removed and optionally washed with water immiscible organic solvent. The organic phase(s) is optionally dried. Concentrating and drying under vacuum yields the product: CAE5-HAE8-γ-CD 1-alkyl-4-hydroxyalkyltriazolium halide salt (or 1-alkyl-2-hydroxyalkyltriazolium halide salt, respectively).

Example 8

Preparation of Sulfoalkylthio ether β-CD N1,N1-(di-(C1-C8 alkyl))-piperidinium halide salt To an aqueous solution of sulfoalkylthio ether-β-CD metal salt (SATE-γ-CD having an ADS of about 5 for the SATE group) is added N1,N1-(di-(C1-C8 alkyl))-piperidinium halide in ethanol. The moles of piperidinium added approximates the ADS of the SATE group of the CD, meaning that for every mole of SATES-β-CD used, that number of moles times 5 (the ADS of the SATE groups) is the approximate number of moles of piperidinium halide used. The batch is stirred overnight. Water immiscible organic solvent is added to the milieu and mixed. The aqueous phase is removed and optionally washed with water immiscible organic solvent. The organic phase(s) is optionally dried. Concentrating and drying under vacuum yields the product: SATES-β-CD N1,N1-(di-(C1-C8 alkyl))-piperidinium salt.

Example 9

Preparation of CAE-HAE-CD 1-alkyl-4-hydroxyalkyltriazolium salt (or 1-alkyl-2-hydroxyalkyltriazolium salt)

To an aqueous solution of CAE5-HAE8-γ-CD metal salt (carboxyalkyl ether-alkyl ether γ-CD having an ADS of about 5 for the CAE group and of about 8 for the HAE group) is added 1-alkyl-4-hydroxyalkyltriazolium halide (or acetate) (or 1-alkyl-2-hydroxyalkyltriazolium halide (or acetate)) in dioxane. The moles of triazolium added approximates the ADS of the CAE group of the CD, meaning that for every mole of CAE5-HAE8-γ-CD used, that number of moles times 5 (the ADS of the CAE groups) is the approximate number of moles of triazolium halide (or acetate) used. The batch is stirred for overnight. Water immiscible organic solvent is added to the milieu and mixed. The aqueous phase is removed and optionally washed with water immiscible organic solvent. The organic phase(s) is optionally dried. Concentrating and drying under vacuum yields the product: CAE5-HAE8-γ-CD 1-alkyl-4-hydroxyalkyltriazolium halide salt (or 1-alkyl-2-hydroxyalkyltriazolium halide salt, respectively).

Example 10

Preparation of CXT-CD N1,N1-(di-C1-C8-alkyl)-N2,N2-(di-C1-C8-alkyl)-N3,N3-(di-C1-C8 alkyl) guanidinium salt)

To an aqueous solution of CXT8-γ-CD metal salt (carboxylated γ-CD having an ADS of about 8 for the CXT group) is added N1,N1-(di-C1-C8-alkyl)-N2,N2-(di-C1-C8-alkyl)-N3,N3-(di-C1-C8 alkyl)guanidinium halide in tetrahydrofuran. The moles of guanidinium added approximates the ADS of the CXT group of the CD, meaning that for every mole of CXT8-γ-CD used, that number of moles times 8 (the ADS of the CXT groups) is the approximate number of moles of guanidinium used. The batch is stirred for overnight. Water immiscible organic solvent is added to the milieu and mixed. The aqueous phase is removed and optionally washed with water immiscible organic solvent. The organic phase(s) is optionally dried. Concentrating and drying under vacuum yields the product: CXT-CD N1,N1-(di-C1-C8-alkyl)-N2,N2-(di-C1-C8-alkyl)-N3,N3-(di-C1-C8 alkyl)guanidinium salt.

Example 11

Preparation of SBE-β-CD 1,3-dialkylimidazolium salt

An exemplary SBE6.2-β-CD is made using the following procedure, wherein the starting beta cyclodextrin parent in an alkaline aqueous medium is derivatized with an SBE precursor in the presence of 1,3-dialkylimidazolium chloride to form the SBE-β-CD. The β CD is dissolved in 11 EQ of 3.7 N NaOH aqueous solution, heated to 50° C., and stirred until complete dissolution. Once dissolution is complete the reaction temperature is increased to 70 to 75° C. 6.8 equivalents of 1,4-Butanesultone is added over a period of 35 minutes. The pH is monitored during the first 4 hours and never dropped below 12.9. The reaction is allowed to continue at 70° C. for at least an addition 16 hours. The reaction mixture is cooled and diluted with water (roughly one half the total reaction volume). The solution is neutralized with 7 M HCl between 6.5 to 7.5 and filtered through a 0.45 micron filter. The solution is purified by Ultrafiltration using a 1000 MWCO membrane. The solution is further treated with carbon (0.12 gram of carbon/gram of cyclodextrin), filtered through a 0.22 micron filter and neutralized (6.5 to 7.0) to yield a solution comprising SBE6.2-β-CD.

The resulting solution is mixed with 1,3-dialkylimidazolium halide, wherein the moles of imidazolium added approximates the ADS of the SBE group of the CD, meaning that for every mole of SBE6.2-β-CD used, that number of moles times 6.2 (the ADS of the SBE groups) is the approximate number of moles of imidazolium used. Water immiscible organic solvent is added to the milieu and mixed. The aqueous phase is removed and optionally washed with water immiscible organic solvent. The organic phase(s) is optionally dried. Concentrating and drying under vacuum yields the product: SBE6.2-β-CD 1,3-dialkylimidazolium salt.

Example 12

Preparation of HP-SBE-β-CD 0.02 mol-cyclodextrin, 0.11 mol NaOH and 45 ml H2O are added into a 3-neck round flask with isobaric funnel, reflux condenser, and thermometer respectively; then stirred to dissolve completely and heated to about 75 deg. C.~80 deg. C. and kept at a constant temperature, and then 0.08 mol 1,4-butane sultone was added within 3 hours, and stirring is continued for about 2 hours, then the solution is cooled down to normal temperature of about 20 deg. C.; 0.08 mol 1,2-propylene oxide is slowly pipetted for about 3 hours; stirring was continued for 5 hours and the pH value is adjusted to neutral with hydrochloric acid; it is filtered and the residual-cyclodextrin and the resultant 1,2-propanediol and sodium-hydroxybutyrate are removed by filtrate dialysis. After 8-10 times of dialysis, the mixture is dried and condensed under reduced pressure conditions, and 25.7 g of white-like solid substance was obtained, yield of 111.7%.

Each value of 1H-NMR spectrum (See annex 12) is analyzed as follows:

| ppm | assignments of proton | Peak characteristics | Peak area | group of proton | DS |
|---|---|---|---|---|---|
| 1.05-1.06 | 3H: —CH$_3$ | d | 5.43 | Hydroxypropyl | 1.8 |
| 1.69 | 4H: —CH$_2$—CH$_2$— | s | 12.02 | sulfobutyl | 3.0 |
| 2.83-2.85 | 2H: —CH$_2$—SO$_3$X | d | 5.99 | Sulfobutyl | 3.0 |
| 3.38-3.91 | 3H: —O—CH$_2$—CH—; 2H: —O—CH$_2$— | m | 53.92 | Glucose ring | |
| 4.99-5.16 | 6H: C$_2$—H; C$_3$—H; C$_4$—H; C$_5$—H; 2 C$_6$—H 1H: —C$_1$H | m | 7.00 | Glucose ring | |

β-CD has seven C1-H (glucose ring C1) with chemical shift of 4.99-5.16 ppm; The integral of the characteristic peak area is 7, which indicates seven C1-H (i.e. one-CD), then the area of the corresponding methyl-peak of the derivative (1.05-1.06 ppm)/3 is the total number of hydroxypropyls connected with methyl in each cyclodextrin (degree of substitution), the corresponding —CH$_2$—CH$_2$— group peak (1.69 ppm) area/4; and the corresponding —CH$_2$—SO$_3$X- group peak (2.83-2.85 ppm) area/2 is the degree of substitution of sulfobutyl group connected in each cyclodextrin. As shown in above table, the degree of substitution of the synthesized product is respectively 1.8 of HP's average degree of substitution and 3.0 of sulfobutyl's average degree of substitution, and was abbreviated as HP2-SBE3-β-CD.

By varying the molar ratios of butane sultone to CD and propylene oxide to CD, a HPm-SBEn-β-CD can be prepared, wherein m ranges from 1 to 9 and n ranges from 1 to 9 and the sum of m+n ranges from 2 to 17 or 2 to 15 or 2 to 12 or 2 to 10.

Example 13

General Procedure for Preparation of HP-SBE-β-CD

Method A.

CD is added with 2-4 times of water by mass and 2-17 times of moles of bases, then added with 2-15 times of 1,4-butyl sultone by mol proportion, and 1.5-13 times of 1,2-propylene oxide by mol proportion. The two reactive reagents are slowly dripped into CD solution, wherein, 2-15 times of bases by mols is required to supplement into the solution that is added with 1,2-propylene oxide, then dripped with the second reagent; wherein, the solution added with 1,4-butyl sultone should react for 5-8 h at the temperature of 80 deg. C.; and the solution added with 1,2 propylene oxide should react for 5-8 h at room temperature to produce the crude product of hydroxypropyl-sulfobutyl-1-cyclodextrin, neutralize the mixture with hydrochloric acid to pH of 6~7, filter, then the filtrate is dialyzed, concentrated to obtain the products by pressure reduction. The following process is recommended:

Method B.

2-4 times of water and 3-17 times molar of NaOH are added to the CD, mixed and heated to 80 deg. C., slowly dripped into 2-15 times of molar ratio of 1,4-butyl sultone, reacted for 5-8 h, cooled down to the room temperature, then slowly dripped 1.5-13 times of molar ratio of 1,2-propylene oxide, reacted for 7-8 h to produce the crude product of hydroxypropyl-sulfobutyl-1-cyclodextrin, then neutralized to pH 6~7 by hydrochloric acid, filtered, then the filtrate is dialyzed, concentrated to obtain the products by pressure reduction.

Method C.

2-4 times of water and 2 times molar of NaOH are added to the CD, mixed and slowly dripped by 1.5-13 times of molar ratio of 1,2-propylene oxide, reacted for 7-8 hours, then supplemented by 2-15 times of molar ratio of NaOH, heated to 80 deg. C., slowly dripped by 2-15 times of molar ratio of 1,4-butyl sultone under constant stirring, reacted for 5-8 h to produce the crude product of hydroxypropyl-sulfobutyl-1-cyclodextrin, then neutralized to pH 6~7 by hydrochloric acid, filtered, then the filtrate is dialyzed, concentrated to obtain the products by pressure reduction.

According to the above synthetic methods, the product having the required degree of substitution can be obtained by different proportion of feeding. The degree of substitution of the products are shown in Table 2.

TABLE 2

Average degree of substitution of 11 kinds of hydroxypropyl-sulfobutyl-β-cyclodestrins

| Product | Average molecular weight (g/ml) | Actual amage degree of substitution* | |
|---|---|---|---|
| | | HP | SEE |
| HP$_1$-SBE4-β-CD | 1756 | 1.2 | 3.5 |
| HP$_2$-SBE$_2$-β-CD | 1620 | 2.1 | 2.3 |
| HP$_2$-SBE$_3$-β-CD | 1713 | 1.8 | 3.0 |
| HP$_3$-SBE$_2$-β-CD | 1616 | 2.7 | 2.1 |
| HP$_3$-SBE$_4$-β-CD | 2000 | 3.2 | 4.3 |
| HP$_3$-SBE$_6$-β-CD | 2171 | 2.6 | 5.6 |
| HP$_4$-SEE$_2$-β-CD | 1676 | 3.9 | 2.0 |
| HP$_4$-SBE$_3$-β-CD | 1799 | 3.8 | 2.8 |
| HP$_5$-SBE$_2$-β-CD | 1677 | 4.6 | 1.8 |
| HP$_5$-SBE$_3$-β-CD | 1923 | 4.9 | 3.2 |
| HP$_6$-SBE$_2$-β-CD | 1720 | 6.0 | 1.5 |

Example 14

The following procedure is used to evaluate the moisture content the cyclodextrin-based ionic liquid.

Determinations are performed in duplicate on 250 mg of each using a Brinkman Karl-Fischer Coulometer (Brinkman Instruments Co., IL). A known weight of ionic liquid is added to the Karl-Fischer Coulometer and the total amount of water in the sample is read-out. This is then converted to a percentage of the solid thus giving the percent moisture content of the sample.

Example 15

Preparation of mixed SBE-β-CD 1,3-dialkyl-3-hydroxyalkylpyrazolium salt and metal salt 1,3-dialkyl-3-hydroxyalkylpyrazolium halide and metal salt of sulfoalkyl ether β-CD (SBE-β-CD) are dissolved in water and optionally heated. The moles of pyrazolium halide are less than the average degree of substitution of the SBE-β-CD, meaning that for every mole of SBE-β-CD used, less than that number of moles times the ADS is the approximate number of moles of pyrazolium halide used. The water is slowly removed under vacuum. Water immiscible or water miscible organic solvent is added to the milieu. Any solid formed (typically the metal halide salt) is filtered off. The filtrate (comprising the SBE-β-CD pyrazolium salt) can be washed with water, water miscible organic solvent or water immiscible organic solvent. The organic phase is optionally dried. Concentrating and drying under a high vacuum yields the product: mixed SBE-β-CD 1,3-dialkyl-3-hydroxyalkylpyrazolium salt and metal salt.

Example 16

Use of SBE-β-CD 1,3-dialkyl-3-hydroxyalkylpyrazolium salt as phase transfer catalyst The above chiral salt, an organic solvent, an alkaline aqueous medium, and dibutyl 1,6-dicarboxy-hexane are mixed in a vessel. 1.0 equivalents (based upon the moles and equivalents of dibutyl 1,6-dicarboxy-hexane) of alkalizing agent, such as sodium hydroxide, is added, optionally with heating. The hydrolysis is allowed to proceed to completion. The mono-esterified butyl 1,6-dicarboxy-hexane is contained within the aqueous phase. The phases are separated. The aqueous phase is acidified with dilute acid to pH 4.5 with cooling. The butyl 1,6-dicarboxy-hexane is isolated by filtration or extraction with diethyl ether.

Example 17

Use of SPE5.4-γ-CD 1,3-dialkylimidazolium salt as chiral extraction medium for selective extraction of steroids from a mixture of steroids A urine sample containing a mixture of steroids (fluticasone propionate and fluticasone) is mixed with the chiral salt above, optionally with an organic solvent, and mixed. The chiral salt-containing phase is separated from the aqueous phase. The chiral salt-containing phase includes fluticasone and excludes any substantial amount of fluticasone propionate.

Example 18

Chirally Selective Extraction of an Enantiomer

[SBE4-EE-β-CD][1,3-dialkylimidazolium] salt (5 mmoles) is mixed with an aqueous solution of racemic drug (balaglitazone (10 mmoles)). The mixture is stirred and allowed to equilibrate. The salt-drug complex is separated from the initial aqueous solution. The content of each enantiomer in the initial aqueous solution and the salt-drug complex is measured by chiral HPLC (J. Chromatography (2004), 1049(1-2), pg. 183-187). A resolution of over 3.0 can be achieved.

The above procedure can be repeated with other drugs such as pioglitazone, rosiglitazone, dihydrophenylalanine, methyldihydroxyphenylalanine, hydrazinomethyl-dihydroxyphenylalanine, baclofen, frovatriptan and other drugs.

Example 19

Supercritical Fluid Extraction of one or more useful compounds from plant mass

A wet or dry ground plant mass containing one or more target compounds is placed in a vessel and mixed with [CAE-γ-CD][1,3-dialkylimidazolium] salt. The vessel is sealed and carbon dioxide is mixed to the vessel. The pressure and temperature within the vessel are approximately 32° C. and 73 bar. The contents of the vessel are stirred and allowed to equilibrate. The carbon dioxide phase is removed from the vessel, and the ionic liquid phase is removed from the vessel. The one or more target compounds is in the carbon dioxide is separated therefrom merely by evaporation of the carbon dioxide, thereby leaving behind a residue containing one or more target compounds, which are the more hydrophobic compounds. The ionic liquid phase can contain one or more target compounds, which are removed from the ionic liquid by extraction with water or buffer at the pH that promotes the highest extraction of the one or more compounds out of the ionic liquid.

The disclosures of the references cited herein are hereby incorporated in their entirety. The term "about" or "approximately" is taken to mean+/−10%, +/−5% or +/−1% of a corresponding or indicated value.

The disclosures of the references cited herein are hereby incorporated herein in their entirety.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A cyclodextrin derivative salt comprising: one or more anionic cyclodextrin derivatives; and one or more cations independently selected at each occurrence from a phosphonium cation or a quaternary nitrogen-containing cation, wherein the quaternary nitrogen-containing cation excludes tetraalkylammonium cation, and wherein each cation is independently substituted or unsubstituted upon each occurrence, provided that when the quaternary nitrogen-containing cation is quaternary ammonium cation, it is of the general formula $(NR_1R_2R_3R)^+$, wherein the radicals $R_1$, $R_2$, and $R_3$ are selected independently at each occurrence from the group consisting of:

substituted linear or branched, saturated or unsaturated, aliphatic or alicyclic alkyl groups with 1 to 20 carbon atoms;

heteroaryl groups, heteroaryl-$C_1$-$C_6$ alkyl groups with 3 to 8 carbon atoms in the heteroaryl radical and at least one heteroatom selected from N, O and S which may be substituted with at least one group selected from $C_1$-$C_6$ alkyl groups and/or halogen atoms;

aryl, aryl-$C_1$-$C_6$ alkyl groups with 5 to 12 carbon atoms in the aryl radical, substituted with at least one $C_1$-$C_6$ alkyl group and/or a halogen atom; and the radical R is selected from the group consisting of:

substituted linear or branched, saturated or unsaturated, aliphatic or alicyclic alkyl groups with 1 to 20 carbon atoms;

heteroaryl-$C_1$-$C_6$ alkyl groups with 3 to 8 carbon atoms in the aryl radical and at least one heteroatom selected from N, O and S, which may be substituted with at least one $C_1$-$C_6$ alkyl group and/or halogen atom;

aryl-$C_1$-$C_6$ alkyl groups with 5 to 12 carbon atoms in the aryl radical, substituted with at least one $C_1$-$C_6$ alkyl group and/or halogen atom; and wherein any two of R, $R_1$, $R_2$, $R_3$ can join together to form a 4- to 8-membered heterocycle including the heteroatom to which each is attached.

2. The cyclodextrin derivative salt of claim 1, wherein the cyclodextrin derivative salt comprises a compound or mixture of compounds of the formula $(Y-Z_m)(cation)$, wherein Y is a cyclodextrin selected from the group consisting of α-cyclodextrin, β-cyclodextrin, and γ-cyclodextrin; and Z is independently selected at each occurrence from an anionic functional group covalently bound to Y; and wherein "m" is in the range of 1 to 18 when Y is an α-cyclodextrin, in the range of 1 to 21 when Y is a β-cyclodextrin, or in the range of 1 to 24 when Y is γ-cyclodextrin, and (cation) is independently selected at each occurrence from the group consisting of phosphonium cation or a quaternary nitrogen-containing cation, wherein the quaternary nitrogen-containing cation excludes tetraalkylammonium cation, and wherein each cation is independently substituted or unsubstituted upon each occurrence.

3. The cyclodextrin derivative salt of claim 2, wherein the anionic functional group is independently selected at each occurrence from the group of sulfonate, sulfate, carboxylate, sulfoalkyl ether, carboxyalkyl ether, phosphate, phosphonate, phosphoalkyl, succinate and a combination thereof.

4. The cyclodextrin derivative salt of claim 2, wherein Y further comprises one or more nonionic (neutral) functional groups covalently bound to the cyclodextrin.

5. A cyclodextrin derivative salt comprising a compound, or mixture of compounds, of the Formula 1,

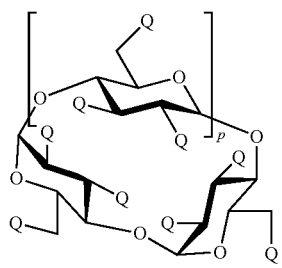

Formula I wherein:
p is 4, 5 or 6;
Q is independently selected at each occurrence from —OH, -sulfoalkyl ether-T, -sulfated alkyl ether-T, -sulfonate-T, -sulfate-T, -carboxyalkyl ether-T, succinylate-T, -sulfoalkylthio ether-T, -carboxylate-T, -phosphoalkyl ether-T, -phosphate-T, and -phosphonate-T, wherein at least one Q is not —OH, and optionally wherein at least one Q is selected from the group consisting of -alkyl ether and -hydroxyalkyl ether; and
T is a cation independently selected at each occurrence from the group consisting of one or more cations independently selected at each occurrence from a phosphonium cation or a quaternary nitrogen-containing cation, wherein the quaternary nitrogen-containing cation excludes tetraalkylammonium cation, and wherein each of the above is independently substituted or unsubstituted upon each occurrence, provided that when the quaternary nitrogen-containing cation is quaternary ammonium cation, it is of the general formula $(NR_1R_2R_3R)^+$, wherein the radicals $R_1$, $R_2$, and $R_3$ are selected independently at each occurrence from the group consisting of:
substituted linear or branched, saturated or unsaturated, aliphatic or alicyclic alkyl groups with 1 to 20 carbon atoms;
heteroaryl groups, heteroaryl-$C_1$-$C_6$ alkyl groups with 3 to 8 carbon atoms in the heteroaryl radical and at least one heteroatom selected from N, O and S which may be substituted with at least one group selected from $C_1$-$C_6$ alkyl groups and/or halogen atoms;
aryl, aryl-$C_1$-$C_6$ alkyl groups with 5 to 12 carbon atoms in the aryl radical, substituted with at least one $C_1$-$C_6$ alkyl group and/or a halogen atom; and
the radical R is selected from the group consisting of:
substituted linear or branched, saturated or unsaturated, aliphatic or alicyclic alkyl groups with 1 to 20 carbon atoms;
heteroaryl-$C_1$-$C_6$ alkyl groups with 3 to 8 carbon atoms in the aryl radical and at least one heteroatom selected from N, O and S, which may be substituted with at least one $C_1$-$C_6$ alkyl group and/or halogen atom;
aryl-$C_1$-$C_6$ alkyl groups with 5 to 12 carbon atoms in the aryl radical, substituted with at least one $C_1$-$C_6$ alkyl group and/or halogen atom; and
wherein any two of R, $R_1$, $R_2$, $R_3$ can join together to form a 4- to 8-membered heterocycle including the heteroatom to which each is attached.

6. The cyclodextrin derivative salt of claim 5 comprising a compound or mixture of compounds, of the formula 1:

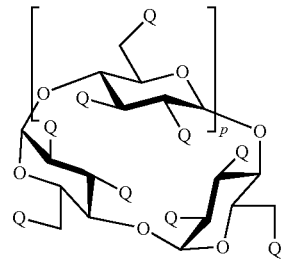

Formula I wherein:
p is 4, 5 or 6;
Q is independently selected at each occurrence from —OH and -sulfoalkyl ether-T, wherein at least one Q is not —OH, and optionally wherein at least one Q is selected from the group consisting of -alkyl ether and -hydroxyalkyl ether;
sulfoalkyl ether is a —O—($C_2$-$C_6$ alkylene)-$SO_3^-$ group, wherein at least one SAE is independently a —O—($C_2$-$C_6$ alkylene)-$SO_3^-$ group, or a —O—$(CH_2)_g SO_3^-$ group, wherein g is 2 to 6; and
T is a cation independently selected at each occurrence from the group consisting of one or more cations independently selected at each occurrence from a phosphonium cation or a quaternary nitrogen-containing cation, wherein the quaternary ammonium cation excludes tetraalkylammonium cation, and wherein each cation above is independently substituted or unsubstituted upon each occurrence.

7. The cyclodextrin derivative salt of claim 1, wherein the quaternary nitrogen-containing cation is independently selected at each occurrence from the group consisting of cationic aromatic heterocycle, cationic non-aromatic heterocycle and quaternary ammonium cation, wherein each cation above is independently substituted or unsubstituted upon each occurrence and wherein the quaternary ammonium cation excludes tetraalkylammonium cation.

8. The cyclodextrin derivative salt of claim 7, wherein the cationic aromatic heterocycle cation is independently selected at each occurrence from the group consisting of acridinium cation, azocinium cation, benzimidazolium cation, benzotriazolinium cation, borazinium cation, cinnolinium cation, 1,2-diazepinium cation, 1,3-diazepinium cation, 1,4-diazepinium cation, benzo-1,2-diazepinium cation, benzo-1,3-diazepinium cation, benzo-1,4-diazepinium cation, benzoxazinium cation, carbazolium cation, imidazolium cation, isoquinolinium cation, indazolium cation, indolium cation, isoindolium cation, nicotinium cation, 1,2,5-oxadiazolinium cation, oxazinium cation, pentazolium cation, phenanthridinium cation, phenanthrolinium cation, purinium cation, pyrimidinium cation, pyridazinium cation, pteridinium cation, purinium cation, pyridinium cation, pyrazinium cation, pyrazolium cation, pyrrolium cation, quinoxalinium cation, quinolinium cation, quinazolinium cation, terpyridinium cation, thiazepinium cation, thiazinium cation, thiazolium cation, triazinium cation, and triazolinium cation, wherein each cation above is independently substituted or unsubstituted upon each occurrence.

9. The cyclodextrin derivative salt of claim 7, wherein the cationic non-aromatic heterocycle cation is independently selected at each occurrence from the group consisting of azetinium cation, azatadinium cation, azepanium cation, azocanium cation, hexamonium cation, indolinium cation, imidazolinium cation, morpholinium cation, oxazolidinium cation, isoxazolidinium cation, pentazolinium cation, piperidinium cation, piperazinium cation, pyrazolidinium cation, pyrrolinium cation, thiazolidinium cation, thiazolinium cation, pyrrolidinium cation, quinolizidinium cation, pyrrolizinium cation, 1,4,7-triazacyclononanium cation and 1,4,7,10-tetrazacyclododecanium cation, wherein each cation above is independently substituted or unsubstituted upon each occurrence.

10. The cyclodextrin derivative salt of claim 1, wherein cation is independently selected at each occurrence from the group consisting of quaternary ammonium cation, imidazolium cation, pyridinium cation, pyrazolium cation, guanidinium cation, phosphonium cation, and triazolium cation, wherein each cation above is independently substituted or unsubstituted upon each occurrence and wherein the quaternary ammonium cation excludes tetraalkylammonium cation.

11. The cyclodextrin derivative salt of claim 1, wherein the anionic cyclodextrin derivative is derivatized with at least two different functional groups other than hydroxyl.

12. The cyclodextrin derivative salt claim 1, wherein the anionic cyclodextrin derivative is independently selected at each occurrence from the group consisting of sulfated alkyl derivatized CD, sulfoalkyl ether derivatized CD, sulfated alkyl ether derivatized CD, sulfonate derivatized CD, sulfate derivatized CD, carboxyalkyl ether derivatized CD, succinylate derivatized CD, sulfoalkylthio ether derivatized CD, sulfoalkyl ether-alkyl ether derivatized CD, sulfoalkyl ether-hydroxyalkyl ether derivatized CD, carboxylate derivatized CD, phosphoalkyl ether derivatized CD, phosphate derivatized CD, phosphonate derivatized CD, carboxyalkyl ether-alkyl ether derivatized CD, carboxyalkyl ether-hydroxyalkyl ether derivatized CD, and a combination thereof.

13. The cyclodextrin derivative salt of claim 12, wherein alkyl is independently selected at each occurrence from a linear or branched, saturated or unsaturated, aliphatic or alicyclic alkyl radical with 1-36 carbon atoms, and the alkyl is non-functionalized or otherwise functionalized with one or more groups selected from the group consisting of an —OH, —OR", —COOH, —COOR", —SO$_4$, —F, —Cl, —Br, —I or —CN, wherein R" is selected from the group consisting of a branched or linear hydrocarbon chain with 1-12 carbon atoms.

14. The cyclodextrin derivative salt of claim 5 comprising a sulfoalkyl ether alkyl ether cyclodextrin compound or mixture of compounds of the formula 4

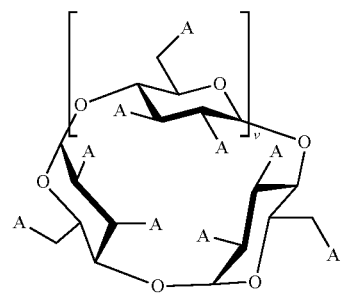

Formula 4 wherein:
"v" is 4, 5 or 6; and
"A" is independently selected at each occurrence from the group consisting of —OH, -(sulfoalkyl ether)x-T and -(alkyl ether)y;
-sulfoalkyl ether is —O—(C$_2$-C$_6$ alkylene)-SO$_3$;
x is the degree of substitution for the -(sulfoalkyl ether)-T moiety and ranges from 1 to 3v+5;
T is a cation independently selected at each occurrence from the group consisting of one or more cations independently selected at each occurrence from a phosphonium cation or a quaternary nitrogen-containing cation, wherein the quaternary nitrogen-containing cation excludes tetraalkylammonium cation, and wherein each cation above is independently substituted or unsubstituted upon each occurrence;
alkyl ether is —O(C$_1$-C$_3$ alkyl); and
y is the degree of substitution for the alkyl ether moiety and ranges from 1 to 3v+5;
provided that at least one -(sulfoalkyl ether)-T moiety and at least one alkyl ether moiety are present; and the sum of x, y and the total number of —OH groups in a cyclodextrin derivative is 3v+6.

15. The cyclodextrin derivative salt of claim 5 comprising a sulfoalkyl ether hydroxyl alkyl ether CD compound, or mixture of compounds, of the formula 5

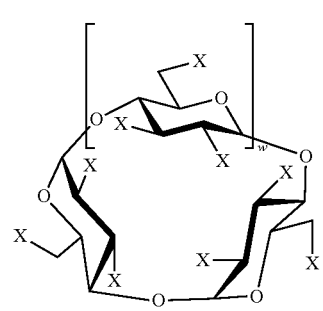

Formula 5 wherein:
"v" is 4, 5 or 6; and
"X" is independently selected at each occurrence from the group consisting of —OH, -(sulfoalkyl ether)x-T and -(hydroxyalkyl ether)y;
x is the degree of substitution for the -(sulfoalkyl ether)-T moiety and is 1 to 3w+5;
-sulfoalkyl ether is —O—(C$_2$-C$_6$ alkylene)-SO$_3$;
T is a cation independently selected at each occurrence from the group consisting of one or more cations independently selected at each occurrence from a phosphonium cation or a quaternary nitrogen-containing cation, wherein the quaternary nitrogen-containing cation excludes tetraalkylammonium cation, and wherein each cation above is independently substituted or unsubstituted upon each occurrence; and hydroxyalkyl ether is HO($C_1$-$C_6$ alkyl)-O—;

y is the degree of substitution for the hydroxyalkyl ether moiety and is 1 to 3w+5;

provided that at least one -(sulfoalkyl ether)-T moiety and at least one -hydroxyalkyl ether moiety are present; and the sum of x, y and the total number of —OH groups in a cyclodextrin derivative is 3w+6.

16. The cyclodextrin derivative salt of claim 14, wherein the quaternary nitrogen-containing cation is independently selected at each occurrence from the group consisting of cationic aromatic heterocycle, cationic non-aromatic heterocycle and quaternary ammonium cation, wherein each cation above is independently substituted or unsubstituted upon each occurrence, and wherein the quaternary ammonium cation excludes tetraalkylammonium cation.

17. The cyclodextrin derivative salt of claim 16, wherein the cationic aromatic heterocycle cation is independently selected at each occurrence from the group consisting of acridinium cation, azocinium cation, benzimidazolium cation, benzotriazolinium cation, borazinium cation, cinnolinium cation, 1,2-diazepinium cation, 1,3-diazepinium cation, 1,4-diazepinium cation, benzo-1,2-diazepinium cation, benzo-1,3-diazepinium cation, benzo-1,4-diazepinium cation, benzoxazinium cation, carbazolium cation, imidazolium cation, isoquinolinium cation, indazolium cation, indolium cation, isoindolium cation, nicotinium cation, 1,2,5-oxadiazolinium cation, oxazinium cation, pentazolium cation, phenanthridinium cation, phenanthrolinium cation, purinium cation, pyrimidinium cation, pyridazinium cation, pteridinium cation, purinium cation, pyridinium cation, pyrazinium cation, pyrazolium cation, pyrrolium cation, quinoxalinium cation, quinolinium cation, quinazolinium cation, terpyridinium cation, thiazepinium cation, thiazinium cation, thiazolium cation, triazinium cation, and triazolinium cation, wherein each cation above is independently substituted or unsubstituted upon each occurrence.

18. The cyclodextrin derivative salt of claim 16, wherein the cationic non-aromatic heterocycle cation is independently selected at each occurrence from the group consisting of azetinium cation, azatadinium cation, azepanium cation, azocanium cation, hexamonium cation, indolinium cation, imidazolinium cation, morpholinium cation, oxazolidinium cation, isoxazolidinium cation, pentazolinium cation, piperidinium cation, piperazinium cation, pyrazolidinium cation, pyrrolinium cation, thiazolidinium cation, thiazolinium cation, pyrrolidinium cation, quinolizidinium cation, pyrrolizinium cation, 1,4,7-triazacyclononanium cation and 1,4,7,10-tetrazacyclododecanium cation, wherein each cation above is independently substituted or unsubstituted upon each occurrence.

19. The cyclodextrin derivative salt of claim 14, wherein cation is independently selected at each occurrence from the group consisting of quaternary ammonium cation, imidazolium cation, pyridinium cation, pyrazolium cation, guanidinium cation, phosphonium cation, and triazolium cation, wherein each cation above is independently substituted or unsubstituted upon each occurrence, and wherein the quaternary ammonium cation excludes tetraalkylammonium cation.

20. The cyclodextrin derivative salt of claim 1, wherein (cation) is selected from the group consisting of:

quaternary ammonium cation with the general formula ($NR_1R_2R_3R$)$^+$, wherein the quaternary ammonium cation excludes tetrabutylammonium tetraalkylammonium cation;

phosphonium cation with the general formula ($PR_1R_2R_3R$)$^+$;

imidazolium cation with the general formula

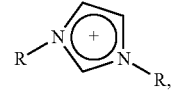

in which the imidazole core may be substituted with at least one group selected from $C_1$-$C_6$ alkyl groups, $C_1$-$C_6$ alkoxy groups, $C_1$-$C_6$ hydroxyalkyl groups, $C_1$-$C_6$ aminoalkyl groups, $C_5$-$C_{12}$ aryl groups or $C_5$-$C_{12}$-aryl-$C_1$-$C_6$ alkyl groups;

pyridinium cation with the general formula

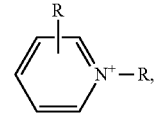

in which a carbon atom of the pyridine core may be substituted with at least one group selected from $C_1$-$C_6$ alkyl group, $C_1$-$C_6$ alkoxy group, $C_1$-$C_6$ hydroxyalkyl groups, $C_1$-$C_6$ aminoalkyl group, $C_5$-$C_{12}$ aryl group or $C_5$-$C_{12}$-aryl-$C_1$-$C_6$ alkyl group;

pyrazolium cation with the general formula

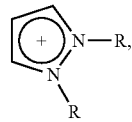

in which a carbon atom of the pyrazole core may be substituted with at least one group selected from $C_1$-$C_6$ alkyl group, $C_1$-$C_6$ alkoxy group, $C_1$-$C_6$ hydroxyalkyl groups, $C_1$-$C_6$ aminoalkyl group, $C_5$-$C_{12}$ aryl group or $C_5$-$C_{12}$-aryl-$C_1$-$C_6$ alkyl group; and triazolium cation with the general formula

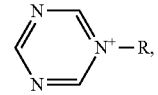

in which a carbon atom of the triazole core may be substituted with at least one group selected from $C_1$-$C_6$ alkyl groups, $C_1$-$C_6$ alkoxy groups, $C_1$-$C_6$ hydroxyalkyl groups, $C_1$-$C_6$ aminoalkyl groups, $C_5$-$C_{12}$ aryl groups or $C_5$-$C_{12}$-aryl-$C_1$-$C_6$ alkyl group; and guanidinium cation with the general formula

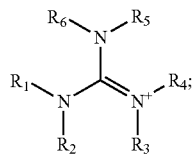

wherein and the radicals $R_1, R_2, R_3, R_4, R_5, R_6$ are selected independently at each occurrence from the group consisting of:
  linear or branched, saturated or unsaturated, aliphatic or alicyclic alkyl groups with 1 to 20 carbon atoms;
  heteroaryl groups, heteroaryl-$C_1$-$C_6$ alkyl groups with 3 to 8 carbon atoms in the heteroaryl radical and at least one heteroatom selected from N, O and S which may be substituted with at least one group selected from $C_1$-$C_6$ alkyl groups and/or halogen atoms;
  aryl, aryl-$C_1$-$C_6$ alkyl groups with 5 to 12 carbon atoms in the aryl radical, which may optionally be substituted with at least one $C_1$-$C_6$ alkyl group and/or a halogen atom; and
the radical R is selected from the group consisting of:
  linear or branched, saturated or unsaturated, aliphatic or alicyclic alkyl groups with 1 to 20 carbon atoms;
  heteroaryl-$C_1$-$C_6$ alkyl groups with 3 to 8 carbon atoms in the aryl radical and at least one heteroatom selected from N, O and S, which may be substituted with at least one $C_1$-$C_6$ alkyl group and/or halogen atom;
  aryl-$C_1$-$C_6$ alkyl groups with 5 to 12 carbon atoms in the aryl radical, which may be substituted with at least one $C_1$-$C_6$ alkyl group and/or halogen atom; and
  wherein any two of R, $R_1, R_2, R_3, R_4, R_5, R_6$ can join together to form a 4- to 8-membered heterocycle including the heteroatom to which each is attached.

21. The cyclodextrin derivative salt of claim 1, wherein
quaternary ammonium cation is independently selected at each occurrence from the group consisting of N1,N1-(di-(C1-C8 alkyl))-piperidinium, N1,N1-(di-(C1-C8 alkyl))-morpholinium, N1,N1-(di-(C1-C8 alkyl))-pyrrolidinium, ethyl-dimethyl-(2-methoxyethyl)ammonium, 1,1-dimethylpyrrolidinium, 1-butyl-1-methylpyrrolidinium, 1-octyl-1-methylpyrrolidinium, 1-hexyl-1-methylpyrrolidinium, 1-(6-aminohexyl)-1-methylpyrrolidinium, 1-(2-methoxyethyl)-1-methylpyrrolidinium, (2-hydroxyethyl) trimethylammonium, 1-(hydrazinocarbonylmethyl)-trimethylammonium, ethyl-dimethyl-(5-diisopropylamino-3-oxapentyl)ammonium, ethyl-dimethyl-cyanomethyl-ammonium, N-(2-methoxyethyl)-N-methyl-morpholinium, 1-(2-methoxyethyl)-1-methyl-piperidinium, 1-(2-methoxyethyl)-1-methyl-pyrrolidinium, 1-butyl-1-methylpyrrolidinium, 1-methyl-1-octyl-pyrrolidinium, 1-methyl-1-hexyl-pyrrolidinium, 1,1-dimethylpyrrolidinium, and 1-(methoxyethyl)-1-methylpyrrolidinium;
imidazolium cation is independently selected at each occurrence from the group consisting of N1-(C1-C8 alkyl)imidazolium, N1-(C1-C8 alkyl)-3-(C1-C8 alkyl)-imidazolium, 1-ethyl-3-methyl-imidazolium, 1,3-dimethyl-imidazolium, 1-propyl-3-methyl-imidazolium, 1-hexyl-3-methyl-imidazolium, 1-octyl-3-methyl-imidazolium, 1-cyanomethyl-3-methyl-imidazolium, 1-benzyl-3-methyl-imidazolium, 1-butyl-3-methyl-imidazolium, 1-butyl-2,3-dimethyl-imidazolium, 1-ethyl-2,3-dimethyl-imidazolium, 1-hexyl-2,3-dimethyl-imidazolium, 1,2,3-(trialkyl)imidazolium, 1,2,3-trimethyl-imidazolium, 1-ethyl-2,3-dimethyl-imidazolium, 1-propyl-2,3-dimethyl-imidazolium, 1-butyl-2,3-dimethyl-imidazolium, 1-hexyl-2,3-dimethyl-imidazolium, and 1-(2-hydroxyethyl)-3-methylimidazolium;
phosphonium cation is independently selected at each occurrence from the group consisting of peralkyl phosphonium, and trihexyl(tetradecyl)phosphonium;
pyridinium cation is independently selected at each occurrence from the group consisting of N—(C1-C8 alkyl)-pyridinium, N-butyl-pyridinium, N-hexyl-pyridinium, N—(C1-C8 alkyl)-(C1-C8 alkyl)pyridinium, N—(C1-C8 alkyl)-(2-, 3- and/or 4-(C1-C8 alkyl)-pyridinium, N-butyl-3-methyl-pyridinium, N-ethyl-3-methyl-pyridinium, N-butyl-4-methyl-pyridinium, N-hexyl-4-dimethylamino-pyridinium, N-ethyl-3-hydroxymethyl-pyridinium, N-(3-hydroxypropyl)-pyridinium, and N-(3-hydroxypropyl)pyridinium;
pyrazolium cation is independently selected at each occurrence from the group consisting of N1-(C1-C8 alkyl)-N2-(C1-C8 alkyl)pyrazolium, and N1-(C1-C8 alkyl)-N2-(C1-C8 alkyl)-(3, 4- and/or 5-(C1-C8 alkyl)-pyrazolium;
triazolium cation is independently selected at each occurrence from the group consisting of N1-(C1-C8 alkyl)-triazolium, and N1-(C1-C8 alkyl)-(2-, 4- and/or 6-(C1-C8 alkyl)-triazolium; or
guanidinium cation is independently selected at each occurrence from the group consisting of peralkylguanidinium, and N1,N1-(di-C1-C8 alkyl)-N2,N2-(di-C1-C8 alkyl)-N3,N3-(di-C1-C8 alkyl)guanidinium,
wherein each of the above is independently substituted or unsubstituted upon each occurrence.

* * * * *